(12) United States Patent
Bennett et al.

(10) Patent No.: US 9,014,775 B2
(45) Date of Patent: *Apr. 21, 2015

(54) MULTI-PARAMETRIC FLUID DETERMINATION SYSTEMS USING COMPLEX ADMITTANCE

(75) Inventors: James W. Bennett, Santa Clara, CA (US); Leonid F. Matsiev, San Jose, CA (US)

(73) Assignee: S.E.A. Medical Systems, Inc., Emerald Hills, CA (US)

( * ) Notice: Subject to any disclaimer, the term of this patent is extended or adjusted under 35 U.S.C. 154(b) by 1023 days.

This patent is subject to a terminal disclaimer.

(21) Appl. No.: 12/875,939

(22) Filed: Sep. 3, 2010

(65) Prior Publication Data

US 2011/0060198 A1      Mar. 10, 2011

Related U.S. Application Data

(63) Continuation-in-part of application No. PCT/US2009/001494, filed on Mar. 9, 2009.

(60) Provisional application No. 61/035,339, filed on Mar. 10, 2008, provisional application No. 61/049,367, filed on Apr. 30, 2008, provisional application No. 61/198,523, filed on Nov. 6, 2008.

(51) Int. Cl.
*A61B 5/05* (2006.01)
*A61B 5/00* (2006.01)
*A61M 31/00* (2006.01)
(Continued)

(52) U.S. Cl.
CPC ........... *A61M 5/168* (2013.01); *A61M 5/16827* (2013.01); *G06F 19/3468* (2013.01); *G01N 21/17* (2013.01); *G01N 27/02* (2013.01); *A61M 2205/331* (2013.01); *A61M 2205/3313* (2013.01); *A61M 2205/3317* (2013.01);
(Continued)

(58) Field of Classification Search
USPC .......... 600/309, 310, 345, 348, 547; 604/500, 604/506, 507, 503, 504
See application file for complete search history.

(56) References Cited

U.S. PATENT DOCUMENTS 3,286,992 A    11/1966    Armeniades et al.
4,029,554 A    6/1977    Ellison
(Continued)

FOREIGN PATENT DOCUMENTS

EP    0499217 B1    1/1996
EP    1739585 A2    1/2007
(Continued)

OTHER PUBLICATIONS

Tian et al, Drug signature using impedance spectroscopy technique, Oct. 13-16, 1999, Proceedings of the First Joint BMES/EMBS Conference, p. 813.*
(Continued)

*Primary Examiner* — Nicholas Lucchesi
*Assistant Examiner* — Shefali Patel
(74) *Attorney, Agent, or Firm* — Shay Glenn LLP

(57) ABSTRACT

An apparatus, systems, and methods related to determining an identity and a concentration of an intravenous fluid. The apparatus, the systems, and the methods described herein may provide near real-time monitoring and/or determination of an identity of components of the intravenous fluid. A concentration and the identity of all of the components of the intravenous fluid may be identified simultaneously.

14 Claims, 18 Drawing Sheets

(51) Int. Cl.

| | |
|---|---|
| *A61M 5/168* | (2006.01) |
| *G06F 19/00* | (2011.01) |
| *G01N 21/17* | (2006.01) |
| *G01N 27/02* | (2006.01) |

(52) U.S. Cl.
CPC .... *A61M2205/3375* (2013.01); *A61M 2205/33* (2013.01); *A61M 2209/02* (2013.01)

(56) References Cited

U.S. PATENT DOCUMENTS

| | | | |
|---|---|---|---|
| 4,132,944 | A | 1/1979 | Bentz |
| 4,601,820 | A | 7/1986 | Leason |
| 4,810,963 | A | 3/1989 | Blake et al. |
| 5,260,665 | A | 11/1993 | Goldberg et al. |
| 5,260,667 | A | 11/1993 | Garcia-Golding et al. |
| 5,425,867 | A | 6/1995 | Dawson et al. |
| 5,569,591 | A | 10/1996 | Kell et al. |
| 5,612,622 | A | 3/1997 | Goldman et al. |
| 5,772,688 | A | 6/1998 | Muroki |
| 5,792,668 | A | 8/1998 | Fuller et al. |
| 5,992,643 | A | 11/1999 | Scrogham et al. |
| 6,028,433 | A | 2/2000 | Cheiky-Zelina et al. |
| 6,182,504 | B1 | 2/2001 | Gaisford |
| 6,449,580 | B1 | 9/2002 | Bardetsky et al. |
| 6,556,001 | B1 | 4/2003 | Wiegand et al. |
| 6,690,181 | B1 | 2/2004 | Dowdeswell et al. |
| 6,771,074 | B2 | 8/2004 | Zou et al. |
| 6,853,203 | B2 | 2/2005 | Beylich et al. |
| 6,885,960 | B2 | 4/2005 | Wagner et al. |
| 6,969,468 | B2 | 11/2005 | Stone et al. |
| 6,970,738 | B1 | 11/2005 | Othman et al. |
| 6,989,680 | B2 | 1/2006 | Sosnowski et al. |
| 6,990,422 | B2 | 1/2006 | Laletin et al. |
| 7,011,631 | B2 | 3/2006 | Davis et al. |
| 7,043,372 | B2 | 5/2006 | Koehler et al. |
| 7,043,402 | B2 | 5/2006 | Phillips et al. |
| 7,049,831 | B2 | 5/2006 | Wooton et al. |
| 7,078,910 | B2 | 7/2006 | Hirthe et al. |
| 7,106,075 | B2 | 9/2006 | Hu |
| 7,109,729 | B2 | 9/2006 | Schilowitz et al. |
| 7,124,120 | B2 | 10/2006 | Wikiel et al. |
| 7,143,637 | B1 | 12/2006 | McBrearty et al. |
| 7,154,102 | B2 | 12/2006 | Poteet et al. |
| 7,218,395 | B2 | 5/2007 | Kaye et al. |
| 7,250,775 | B1 | 7/2007 | Collins et al. |
| 7,253,644 | B2 | 8/2007 | Song |
| 7,270,733 | B2 | 9/2007 | Wikiel et al. |
| 7,315,767 | B2 | 1/2008 | Caduff et al. |
| 7,317,525 | B2 | 1/2008 | Rzasa et al. |
| 7,465,425 | B1 | 12/2008 | Sun |
| 7,474,971 | B2 | 1/2009 | Hu et al. |
| 7,581,434 | B1 | 9/2009 | Discenzo et al. |
| 7,621,181 | B2 | 11/2009 | Cammarata et al. |
| 7,696,763 | B1 | 4/2010 | Sun |
| 8,328,082 | B1 | 12/2012 | Bochenko et al. |
| 8,355,753 | B2 | 1/2013 | Bochenko et al. |
| 8,385,972 | B2 | 2/2013 | Bochenko et al. |
| 8,394,053 | B2 | 3/2013 | Bochenko et al. |
| 2002/0180570 | A1 | 12/2002 | Facer et al. |
| 2002/0183693 | A1 | 12/2002 | Peterson et al. |
| 2003/0048432 | A1 | 3/2003 | Jeng et al. |
| 2003/0072549 | A1 | 4/2003 | Facer et al. |
| 2003/0159741 | A1 | 8/2003 | Sparks |
| 2003/0204330 | A1 | 10/2003 | Allgeyer |
| 2004/0012395 | A1 | 1/2004 | Salamitou |
| 2004/0020772 | A1 | 2/2004 | Bas et al. |
| 2004/0058385 | A1 | 3/2004 | Abel et al. |
| 2004/0079652 | A1 | 4/2004 | Vreeke et al. |
| 2004/0126814 | A1 | 7/2004 | Singh et al. |
| 2004/0142405 | A1 | 7/2004 | Alfonta et al. |
| 2004/0171983 | A1 | 9/2004 | Sparks et al. |
| 2005/0023155 | A1 | 2/2005 | Sawyer et al. |
| 2005/0266582 | A1 | 12/2005 | Modlin et al. |
| 2006/0105467 | A1 | 5/2006 | Niksa et al. |
| 2007/0072286 | A1 | 3/2007 | Orsel et al. |
| 2007/0191700 | A1 | 8/2007 | Say et al. |
| 2007/0293817 | A1* | 12/2007 | Feng et al. ............... 604/65 |
| 2008/0053202 | A1 | 3/2008 | Rohklin et al. |
| 2008/0105565 | A1 | 5/2008 | Davalos et al. |
| 2008/0116908 | A1 | 5/2008 | Potyrailo et al. |
| 2008/0167823 | A1 | 7/2008 | Koehler et al. |
| 2008/0172187 | A1 | 7/2008 | Koehler et al. |
| 2009/0102450 | A1 | 4/2009 | Da Silva et al. |
| 2009/0115435 | A1 | 5/2009 | Tomlinson |
| 2009/0115436 | A1 | 5/2009 | Koehler, III et al. |
| 2009/0261847 | A1 | 10/2009 | Petrovsky et al. |
| 2009/0293590 | A1 | 12/2009 | Zeng et al. |
| 2010/0300899 | A1 | 12/2010 | Levine et al. |
| 2011/0089050 | A1 | 4/2011 | Albu et al. |
| 2011/0111985 | A1 | 5/2011 | Lakey et al. |
| 2012/0037266 | A1 | 2/2012 | Bochenko |
| 2012/0065617 | A1 | 3/2012 | Matsiev et al. |
| 2012/0115248 | A1 | 5/2012 | Ansyln et al. |
| 2012/0287431 | A1 | 11/2012 | Matsiev et al. |
| 2013/0204227 | A1 | 8/2013 | Bochenko et al. |
| 2014/0249503 | A1 | 9/2014 | Bennett et al. |

FOREIGN PATENT DOCUMENTS

| | | |
|---|---|---|
| EP | 2042719 A2 | 4/2009 |
| EP | 2068139 A1 | 6/2009 |
| JP | 2006-138770 | 6/2006 |
| JP | 2008-003046 | 1/2008 |
| JP | 2008-76227 | 4/2008 |
| WO | WO2004/033003 A1 | 4/2004 |
| WO | WO2005/007223 A2 | 1/2005 |
| WO | WO2006/010310 A1 | 2/2006 |
| WO | WO2006/101290 A1 | 9/2006 |
| WO | WO2007/047004 A2 | 4/2007 |
| WO | WO2007/054700 A1 | 5/2007 |
| WO | WO2008/073931 A2 | 6/2008 |
| WO | WO2008/133656 A2 | 11/2008 |
| WO | WO2008131609 A1 | 11/2008 |

OTHER PUBLICATIONS

Tian et al, Drug signature using impedance spectroscopy technique, Oct. 13-16, 1999, Proceedings of the First Joint BMES/EMBS Conference, p. 813.*
Bow, Sing-Tze; Pattern Recognition and Image Preprocessing; 2nd ed.; Marcel Dekker; pp. 16-20, 29-32, 112-117, 197-199, and 511-513 (21 total pgs.); 2002.
Bruun, H. H.; Hot-wire anemometry: principles and signal analysis; Oxford University Press; pp. 34-37 & 112-121 (14 total pgs); 1995.
Cole-Parmer (Tech. Library); Why Measure Viscosity? What is it?; 10 pgs.; printed Sep. 8, 2010 (http://www.coleparmer.com/techinfo/techinfo.asp?htmlfile=why-meas-viscosity.htm&ID=933).
Endress+Hauser; Bubble Detection Sensor OUSAFI3; Tech. Info. Doc. No. TI921C/24/ae; 4 pgs.; printed/accessed Sep. 10, 2010 (https://portal.endress.com/wa001/dla/50001951410/000/00/T1921CAE.pdf).
Fouke et al.; Sensor for measuring surface fluid conductivity in vivo; IEEE Trans Biomed Eng.; vol. 35; No. 10; pp. 877-881; Oct. 1988.
Gonzalez et al.; Fluid flow induced by nonuniform ac electric fields in electrolytes on microelectrodes. ii. a linear double-layer analysis; Phys. Rev. E; vol. 61; No. 4; pp. 4019R4028; Apr. 2000.
Green et al.; Fluid flow induced by nonuniform ac electric fields in electrolytes on microelectrodes. i. experimental measurements; Phys. Rev. E; vol. 61; No. 4; pp. 4011R4018; Apr. 2000.
Green et al.; Fluid flow induced by nonuniform ac electric fields in electrolytes on microelectrodes. iii. observation of streamlines and numerical simulation; Phys. Rev. E; 66; 026305; 2002.
Green et al.; Impedance based flow sensors; Microtechnologies for the New Millennium; 2005 SPIE; May 9-11, 2005.
Helmholtz; Studien über elektrische Grenzschichten. Annalen der Physik und Chemie; Neue Folge; 7 (7), p. 337-382; 1879—(translation: P. E. Bocque; Studies of electric boundary layers; Dep. Engineering Research Univ. Mich.; 33; pp. 5-47; 1951).
Homola, Jiri (Ed.); Surface Plasmon Resonance Based Sensors; Springer Series on Chemical Sensors and Biosensors; vol. 4; pp. 134-138; 2006.

(56) References Cited

OTHER PUBLICATIONS

Kikutani et al.; Flowing thermal lens micro-flow velocimeter; Sensors and Actuators B: Chemical; vol. 133; iss. 1; pp. 91-96; Jul. 28, 2008.
Krasser et al.; Simultaneous Measurements at U-tube Density Sensors in Fundamental and Harmonic Oscillation; EUROCON; The Int'l Conf. on "Computer as a tool"; pp. 551-555; Sep. 9-12, 2007.
Kumar et al.; A fibre optic evanescent wave sensor used for the detection of trace nitrites in water; Journal of Optics A: Pure and Applied Optics; vol. 4; pp. 247-250; 2002.
MacDonald et al.; Analysis of impedance and admittance data for solids and liquids; J. Electrochem. Soc.; vol. 124; No. 7; pp. 1022-1030; 1977.
MacDonald; Impedance spectroscopy-emphasizing solid materials and systems; 1st ed.; John Wiley and Sons; pp. 1-4; 1987.
MacDonald; Theory of ac space-charge polarization effects in photoconductors, semiconductors, and electrolytes; Physical Review; vol. 92; No. 1; pp. 4-17; 1953.
Maltoni et al.; Handbook of Fingerprint Recognition; Springer, NY; pp. 137-141; 2003.
Mathioulakis et al.; A pulsed-wire technique for velocity and temperature measurements in natural convection flows; Experiments in Fluids; vol. 18; Nos. 1-2; pp. 82-86; Dec. 1994.
Nixon, M.S. et al.; Feature Extraction and Image Processing; 1st ed.; MPG Books Ltd.; pp. 164-169; 2002.
Oh et al.; Minimization of electrode polarization effect by nanogap electrodes for biosensor applications; The 16th Ann Int'l Conf on Micro Electro Mech Sys 2003; MEMS-03 Kyoto. IEEE; pp. 52-55; Jan. 19-23, 2003.
Omega Engineering; Turbidity Measurement; 4 pgs.; printed/accessed Sep. 10, 2010 (http://www.omega.com/techref/ph-6.html).
Optek; Inline process color measurement (Application note from website; 2 pgs.; printed Sep. 8, 2010 (http://www.optek.com/Application_Note/General/English/7/Inline_Process_Color_Measureme nt.asp).
Orazem et al.; History of Impedance Spectroscopy; Electrochemical Impedance Spectroscopy; John Wiley & Sons; pp. XXV-XXXI; (published online) Feb. 7, 2008.
Potyrailo et al.; Near-Ultraviolet Evanescent-Wave Absorption Sensor Based on a Multimode Optical Fiber; Anal. Chem.; vol. 70; No. 8; pp. 1639R1645; 1998.
Resonance; ElectroChemical Methods; 11 pgs.; printed/accessed from archive Sep. 10, 2010 (http://web.archive.org/web/20061023171937/http://www.resonancepub.com/electrochem.htm).
Richter, Andreas; Differential optical absorption spectroscopy as a tool to measure pollution from space; Spectroscopy Europe; vol. 18; No. 6; pp. 14-21; 2006.
Sarmousakis et al.; Impedance at polarized platinum electrodes in various electrolytes; Journal of the Electrochemical Society; vol. 104; No. 7; pp. 454-459; 1957.
Schirmer et al.; A new method for the determination of membrane permeability by spatially resolved concentration measurements; Meas. Sci. Technol.; vol. 15; No. 9; pp. 195-202; 2004.
Schwan; Linear and nonlinearelectrode polarization and biological materials; Ann. Biomed. Eng.; vol. 20; pp. 269-288; 1992.
Sensorland.com; How Sensors Work—Understanding pH measurement; 7 pgs.; printed Sep. 8, 2010 (http://www.sensorland.com/HowPage037.html).
Singh, Shyam; Refractive Index Measurement and its Applications; Physica Scripta; vol. 65; No. 2; pp. 167-180; 2002.
Stachowiak et al.; A thermoelectric sensor for fluid flow measurement. principles, calibration and solution for self temperature compensation; Flow Measurement and Instrumentation; vol. 9; iss. 3; pp. 135-141; Sep. 1998.
Test & Measurement World; Analysis of dielectric material properties using LCR meters; www.tmworld.com/contents/pdf/tmw03_05D1_jr.doc; printed/accessed Oct. 26, 2010.
Walton et al.; Platinum pacemaker electrodes: origins and effects of the electrode-tissue interface impedance; Pacing Clin. Electrophysiol; vol. 10; pp. 87R99; 1978.
Way et al.; Hot-wire probes for measuring velocity and concentration in helium-air mixtures; AIAA Journal; vol. 8; No. 5; pp. 976R978; 1970.
Bennett et al.; U.S. Appl. No. 12/920,203 entitled "Intravenous Fluid Monitoring," filed Aug. 30, 2010.
Matsiev et al.; U.S. Appl. No. 12/796,567 entitled "Systems and Methods for the Identification of Coumpounds in Medical Fluids Using Admittance Spectroscopy," filed Jun. 8, 2010.
Tian et al.; Drug signature using impedance spectroscopy technique; BMES/EMBS Proc. Of the First Joint Conf., Atlanta, Georgia; vol. 2; pp. 813; Oct. 13, 1999.
Bauerle, J.E.; Study of solid electrolyte polarization by a complex admittance method: J. of Physics and Chem. of Solids; vol. 30; No. 12; pp. 2657-2670; Dec. 1969.
Carter, C.W.; Graphic Representation of the impedance of networks containing resistance and two reactances: Bell Sys. Tech. J.;vol. 4; pp. 387-401; Jul. 1925.
Cole et al.; Dispersion and absorption in dielectrics I. alternation current characteristics: J. Chem. Phys.;vol. 9 No. 4; pp. 341-351; Apr. 1941.
Fischler et al.; Polarisation impedance of pacemaker electrodes: in vitro studies simulating practical operation; Med. Biol. Eng. and Comput.; vol. 19; No. 5; pp. 579-588; Sep. 1981.
Sluyters J.H.; On the impedance of galvanic cells: I. Theory.; Rec. Trav Chim.; vol. 79; No. 10; pp. 1092-1100; (the year of publication is sufficiently earlier than the effective U.S. filed and any foreign priority date) 1960.
Sluyters J.H.; On the impedance of galvanic cells: II. Experimental verification.; Rec. Trav Chim.; vol. 79; No. 10; pp. 1101-1110; (the year of publication is sufficiently earlier than the effective U.S. filed and any foreign priority date) 1960.
Smith, P.H.; An improved transmission line calculator; Electronics.; vol. 17; No. 1; pp. 130-133; Jan. 1944.
Smith, P.H.; Transmission line calculator; Electronics.; pp. 29-31; Jan. 1939.
MacDonald et al.; Fundamentals of Impedance Spectroscopy (Ch. 1/pp. 1-4); in Impedance Spectroscopy: Theory, Experiment, and Applications 2nd Ed.; Barsoukov & MacDonald; pp. 1-4; Mar. 2005.
Überall, Herbert; Interference and Steady-State Scattering of Sound Waves; In: Handbook of Acoustics (M. J. Crocker (Ed.); Chap. 4; pp. 47-60; Mar. 1998.
Cohen et al.; U.S. Appl. No. 14/054,744 entitled "Devices, Systems and Methods for Determining Drug Composition and Volume," filed Oct. 15, 2013.

* cited by examiner

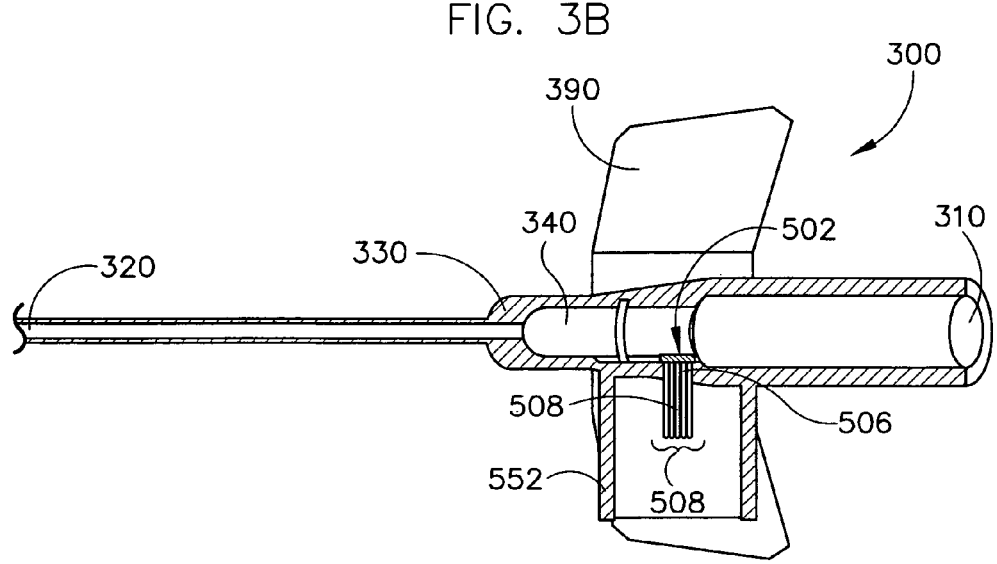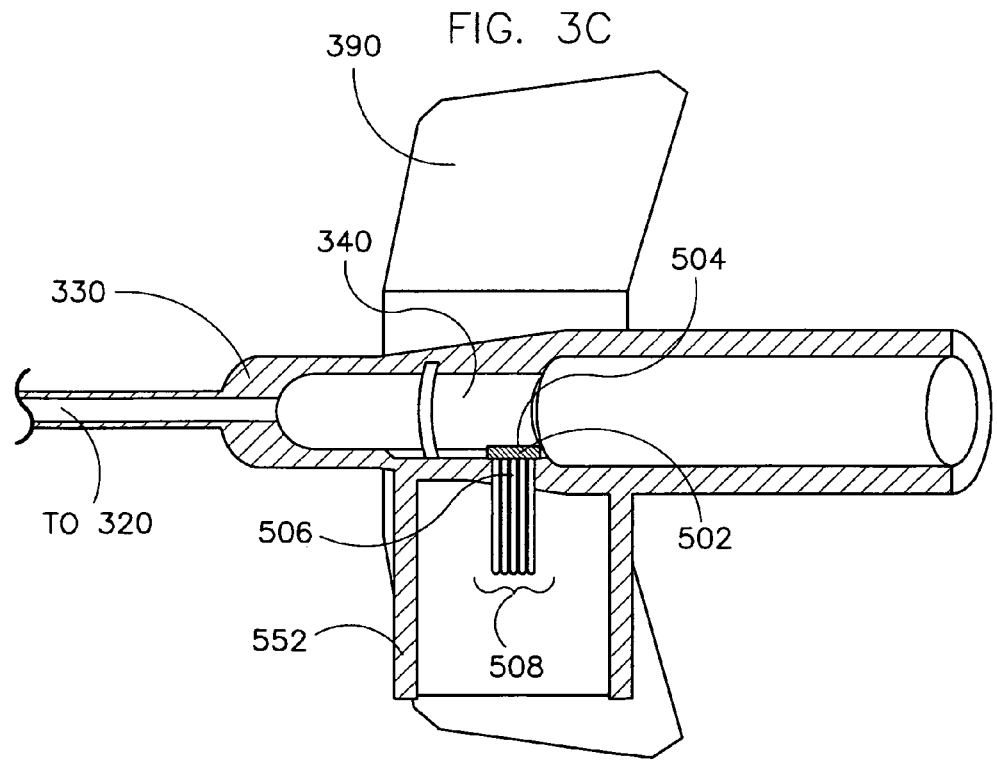

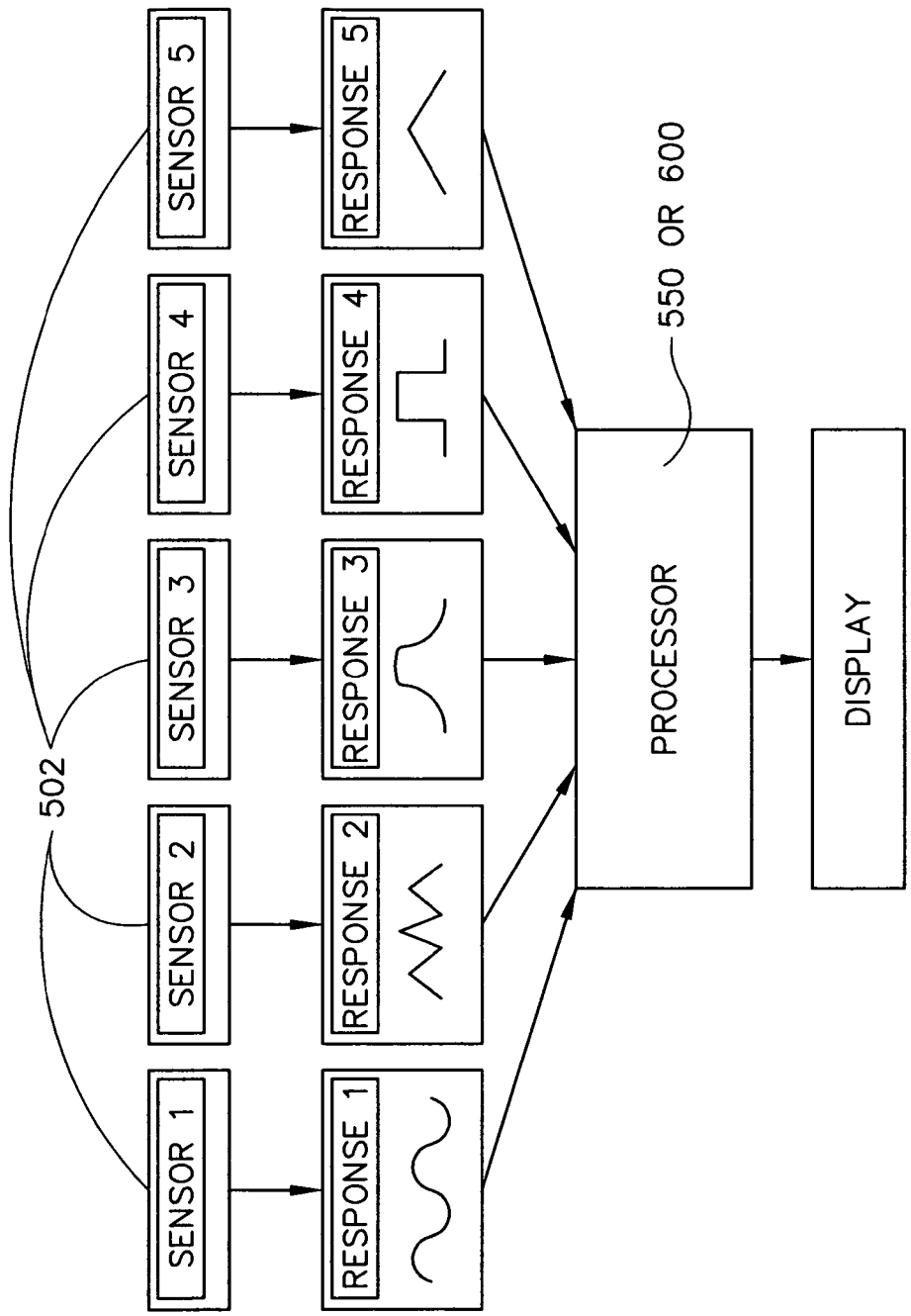

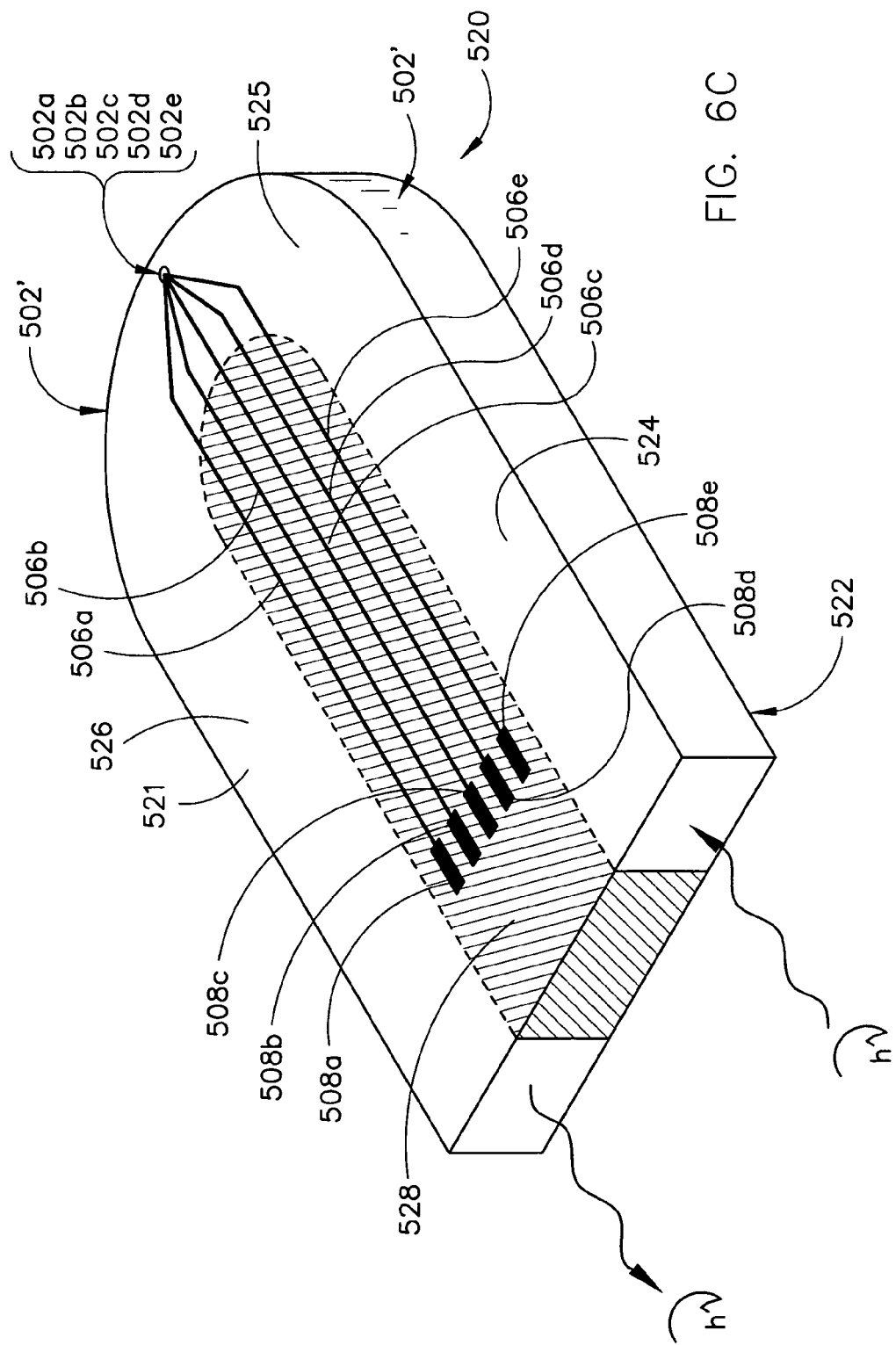

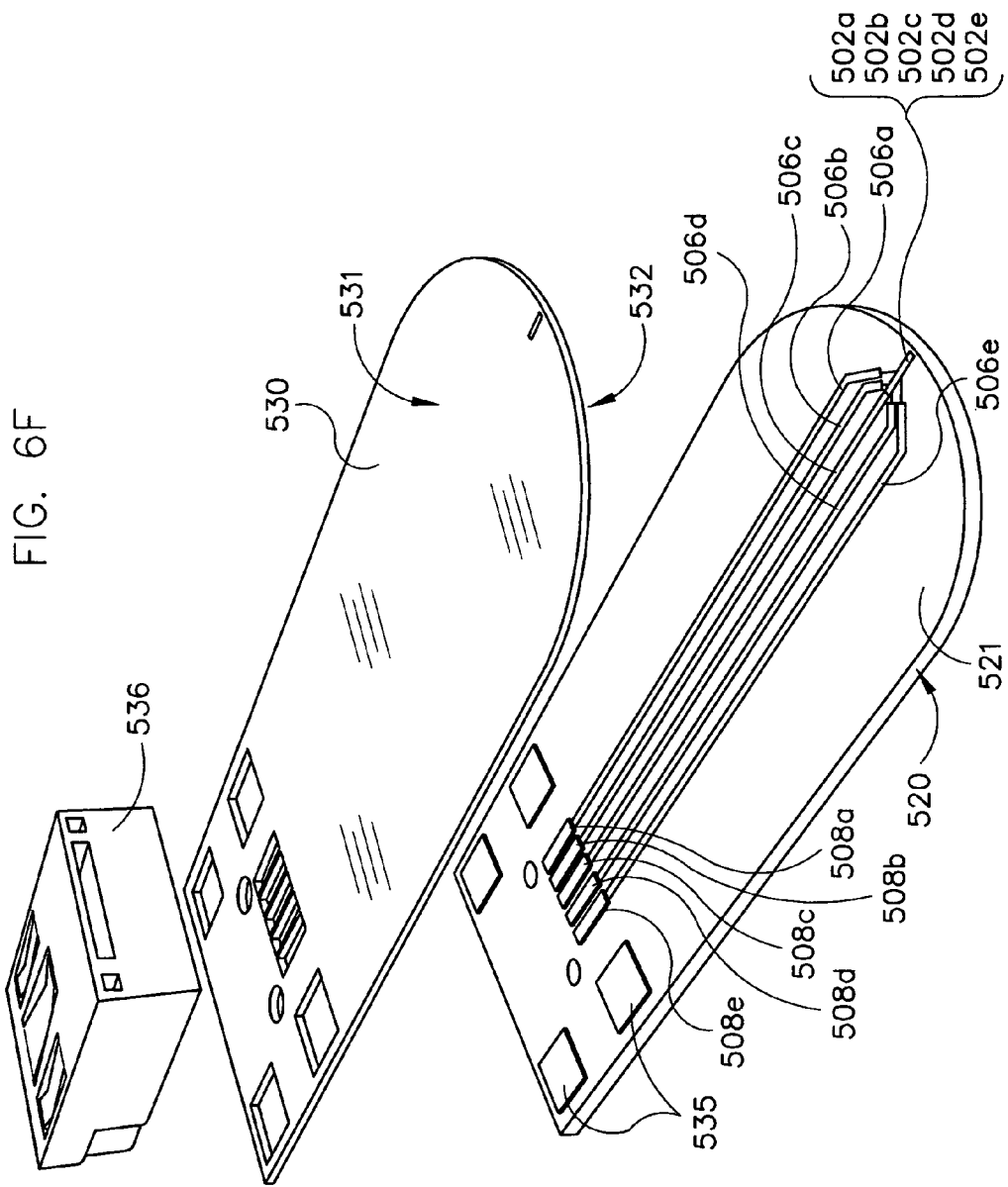

MULTI-PARAMETRIC FLUID DETERMINATION SYSTEMS USING COMPLEX ADMITTANCE

CROSS REFERENCE TO RELATED APPLICATIONS

The present application is a continuation-in-part of International Application No. PCT/US2009/001494 (International Publication No. WO 2009/114115), with an international filing date of Mar. 9, 2009, which application claims priority to the following U.S. provisional applications: Appln. No. 61/035,339 filed Mar. 10, 2008; Appln. No. 61/049,367 filed Apr. 30, 2008; and Appln. No. 61/198,523 filed Nov. 6, 2008, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

This application relates to the field of intravenous fluid identification and verification.

BACKGROUND OF THE INVENTION

The invention relates to intravenous fluid monitoring apparatus, systems and methods. In particular, the invention relates to intravenous fluid monitoring apparatus and systems comprising sensors for identifying one or more components of an intravenous fluid, and to methods for intravenous delivery of fluid to a subject including sensing of the fluid during administration to the subject.

Intravenous fluid delivery systems and methods are known in the art. Such systems can generally comprise an intravenous infusion device (e.g., such as a cannula or a catheter) for infusion of fluid into the vasculature system of a subject in need thereof (e.g., a patient), one or more fluid sources for containing an intravenous fluid or a component thereof, and an fluid line assembly providing fluid communication between the one or more fluid sources and the intravenous infusion device. Known systems include multiple arrangements and configurations, including, generally for example various systems (e.g., gravity-feed systems; pump systems) for providing a motive force for delivery of the fluid from the source to the subject, as well as various further components typically integrated into the fluid line assembly such as conduits, fittings (e.g., Luer Lock™ fittings), backflow blocks, valves, and injection ports.

Some intravenous fluid delivery systems known in the art also include one or more sensors, such as flow sensors (to measure a precise amount of a fluid being delivered), pressure sensors (e.g., to detect fluid line blockage) and/or ultrasonic sensors (e.g., to detect air-bubbles). See, for example, U.S. Patent Application No. US 2003/0159741 to Sparks.

Notwithstanding the various advances known in the art in connection with intravenous fluid delivery, there remains a need in the art for improvements, especially improvements which enhance the accuracy and/or reliability of treatments involving intravenous fluid delivery to patients, and correspondingly which enhance patient safety. In particular, there remains a need for improvements in sensing, monitoring and recording the identity of fluid compositions (e.g., component identity, component concentration, component dose (e.g., current, projected) etc.) being delivered to patients in the course of treatment.

SUMMARY OF THE INVENTION

The present inventions provide apparatus, systems and methods related to intravenous fluid verification, identification and/or characterization. In particular, the apparatus, systems and methods herein relate to intravenous fluid characterization using complex admittance. The apparatus, systems and methods of the invention are may be used for monitoring of intravenous fluids during administration to a subject. As described herein and in further detail below, the various inventions offer intravenous fluid monitoring approaches which are significantly advantaged over known systems, including for example by providing near real-time monitoring of the identity of one or more components of an intravenous fluid (e.g., the presence or absence of a component, the composition of a component, the concentration of a component, the time (absolute time or relative time versus other components) of infusion of a component, the onset of component infusion (i.e., delivery through an infusion device); the completion of component infusion, the component dosing level (e.g., cumulative dosing level—current or projected), etc.). Such near real-time monitoring of intravenous fluids reduces the potential for errors associated with intravenous administration, and especially intravenous drug administration. Hence, the apparatus, systems and methods of the invention provide substantial advances in patient safety. Such advances in safety can translate to a more meaningful patient treatment experience, and to enhanced operational efficiencies and reduced expenses for hospitals and other entities which administer fluids intravenously. Such inventions can applied, and such advantages can be realized in a number of various settings and applications in which intravenous fluids are administered, including for example, without limitation, at hospitals, clinics, surgical centers, homes (e.g., home hospice), nursing homes, assisted living environments, etc.

Generally, the apparatus, systems and methods of the invention are directed to or effective for identifying one or more components of an intravenous fluid during administration of the fluid to a subject. Preferably, the apparatus, systems and methods of the invention are directed to or effective for identifying one or more active pharmaceutical agents within an intravenous fluid during administration of the fluid to a subject. Such active pharmaceutical agents can include, for example, an anticoagulant (e.g., heparin), a metabolically-active hormone (e.g., insulin), an anesthetic (e.g., propofol), and/or an analgesic (e.g., morphine), among others. Additionally or alternatively, the apparatus, systems and methods of the invention are directed to or effective for identifying one or more other components of an intravenous fluid, preferably components used for hydration and ion metastasis of subjects. Such components can preferably include, for example one or more components selected from potassium chloride, sodium chloride, Ringer's lactate, and dextrose, in each case in molecular or ionic (e.g., dissociated) form (e.g., sodium ion, potassium ion, chloride ion, calcium ion, lactate ion, and dextrose).

Generally, and preferably, the apparatus, systems and methods of the invention are directed to or effective for identifying one or more components of an intravenous fluid during administration of the fluid to a subject using a multi-parametric approach. In such approach, multiple parameters (e.g., multiple fluid properties such as without limitation refractive index, electrochemical potential, impedance, admittance, conductivity, etc.) can be sensed, and the combination of parameters can be correlated to obtain resolution of components within the fluid. Hence, an intravenous fluid can be sensed—for example with multiple sensors (or with a sensor having multiple sensor elements) and/or with multiplexing of a sensor element to obtain independent sensing measurements—to generate a multi-parametric profile characteristic of component identity within the fluid. A multi-parametric profile can be correlated to determine an identity of one or more components of the fluid. Such multi-parametric approaches advantageously provide for improved resolution of components; therefore such approaches allow for improved ability to distinguish between different fluid compositions, including for example the presence or absence of particular active pharmaceuticals, and/or various concentrations of a particular active pharmaceutical or other component. Multi-parametric approaches as described herein are preferred, an can be generally used with any aspects, embodiments and approaches described herein; however, many aspects, embodiments and approaches of the invention do not require multi-parametric approaches and can be effected independently thereof.

Generally, and preferably, the apparatus, systems and methods of the invention are directed to or effective for identifying one or more components of an intravenous fluid during administration of the fluid to a subject using one or more sensors. The one or more sensors are preferably selected to include at least one sensor other than a flow sensor, and/or in some embodiments also preferably other than a pressure sensor, and/or in some embodiments also preferably other than an ultrasonic sensor. Generally for example, preferred sensors effective with the apparatus, systems and methods of the invention can include, without limitation, one or more sensors selected from an impedance sensor (e.g., an AC impedance spectroscopy sensor), an electrochemical sensor (e.g., an electrochemical potential sensor), a thermal sensor (e.g., a thermal anemometer sensor), an optical sensor (e.g., a refractometer sensor, a transmission sensor, an absorbance sensor, a spectrometer (including a colorimeter) or, a turbidity sensor), a rheological sensor (e.g., a viscometer), an electrical property sensor (e.g., a capacitor sensor, a pH sensor, a conductivity sensor, and an inductive sensor), and a fluid-displacing and/or fluid-shearing (e.g., resonator) sensor. In various preferred embodiments, the sensors can be one or more sensors selected from an impedance sensor (e.g., an AC impedance spectroscopy sensor) and an optical sensor (e.g., a refractometry sensor, a transmission sensor, an absorbance sensor, a spectrometer (including a colorimeter) or, a turbidity sensor). In certain preferred embodiments, the apparatus, systems and methods of the invention comprise or use at least two or more sensors or an integrated assembly comprising two or more sensors (e.g., an integrated assembly comprising two or more sensor elements, each sensor element comprising one or more sensing surfaces), and preferably such two or more sensors being of different types and/or having different sensor approaches (e.g., impedance sensor, electrical property sensor, optical sensor, etc.). Preferably, such two or more sensors can include an impedance sensor (e.g., an AC impedance spectroscopy sensor), a thermal sensor, and/or an optical sensor (e.g., a refractometry sensor, a transmission sensor, an absorbance sensor, a spectrometer (including a colorimeter) or, a turbidity sensor). Preferably, such two or more sensors can be integrated into a common assembly, such as a common substrate, e.g., as part of a common sensor subunit. For example, the apparatus, systems and methods of the invention comprise an impedance sensor (e.g., an AC impedance spectroscopy sensor) and an optical sensor (e.g., a refractometry sensor), each integral with and/or in a common sensor assembly such as a common substrate, or a common sensor subunit. The various specific sensors and sensing approaches as described herein are preferred, an can be generally used with any aspects, embodiments and approaches described herein; however, many aspects, embodiments and approaches of the invention do not require such certain specific sensors or sensing techniques and can be effected independently thereof.

Generally, and preferably, the apparatus, systems and methods of the invention are directed to or effective for identifying one or more components of an intravenous fluid during administration of the fluid to a subject using a sensor having a sensor element (e.g., with a sensing surface adapted for interaction with and being responsive to the intravenous fluid), where such sensor element (e.g., such sensing surface) is positioned at a location within an intravenous fluid system such that it interacts with the fluid (e.g., such sensing surface contacts the fluid) in relative proximity to the infusion location—the location at which the fluid enters a subject's vasculature system. Advantageously, monitoring of intravenous fluids proximal to the infusion location (e.g., proximal to the distal end of a fluid line assembly of an intravenous fluid delivery system, and/or proximal to an infusion device of an intravenous fluid delivery system) can effectively reduce the potential for errors associated with intravenous administration. Such proximity is less constrained by physical distance; rather it more generally refers to a location within an intravenous fluid delivery system at which the composition of the intravenous fluid is representative of (if not identical to) that which is delivered to the subject. Hence, such proximity typically refers to a position or location within the intravenous fluid delivery system which is downstream relative to various components of the intravenous fluid delivery system which could change or otherwise effect the fluid identity (e.g., composition, concentration etc), including for example downstream of infusion valves, injection ports, supply line junctions, etc. In various embodiments of various aspects of the invention, therefore, the apparatus, systems and methods of the invention comprise a sensor element (e.g., having a sensor surface) positioned proximal to (e.g., at or near) the distal end of a fluid line assembly, and/or proximal to an infusion device. For example, such a sensor element can include a sensing surface in a cavity of an in-line housing, where the in-line housing optionally has inlet and outlet fittings (e.g., luer locks), and can be integrated into the fluid line assembly upstream of an infusion device. Alternatively, for example, such a sensor element can include a sensing surface in a cavity of a housing defined in infusion device (e.g., catheter, needle, etc.). Further, in some embodiments, in addition to one or more sensors positioned for monitoring of intravenous fluids proximal to the infusion location (e.g., proximal to the distal end of a fluid line assembly and/or proximal to an infusion device), the apparatus, systems and method of the invention can also include an additional sensor positioned upstream of an injection port—facilitating for example a differential measurement approach. The approaches for positioning of the sensor element proximal to the infusion location, as described and as variously exemplified herein are preferred, and can be generally used with any aspects, embodiments and approaches described herein; however, many aspects, embodiments and approaches of the invention do not require such certain specific positioning approaches and can be effected independently thereof.

Generally, and preferably, the apparatus, systems and methods of the invention are directed to or effective for identifying one or more components of an intravenous fluid during administration of the fluid to a subject (e.g., a specific patient, for example at a hospital, clinic, surgical environment, home hospice, nursing home, assisted living environment, etc), where such subject is positively and specifically identified in connection with monitoring and administration of the intravenous fluid. Various embodiments and aspects of the invention can include approaches for correlating the sensor data (i.e., data (e.g., as represented by a signal) originating from the sensor—either raw data or more typically processed data) to a specific subject (e.g., patient). For example, the sensor (or apparatus or system comprising a sensor) can include an identifier circuit for correlating sensor data to a specific subject. Typically, and preferably, such identifier circuit may be in communication with one or more other circuits, including for example circuits for receiving processing, storing, displaying or transmitting data, including data originating from the sensor element, such as a signal processing circuit or a data retrieval circuit. Such integrated patient-identification approaches can further enhance the benefit to patient safety, by reducing the potential for errors associated with intravenous administration, and especially intravenous drug administration. The various subject-identifier approaches as described herein are preferred, an can be generally used with any aspects, embodiments and approaches described herein; however, many aspects, embodiments and approaches of the invention do not require such certain specific subject-identifier approaches and can be effected independently thereof.

Generally, and preferably, the apparatus, systems and methods of the invention are directed to or effective for identifying one or more components of an intravenous fluid during administration of the fluid to a subject with a remote and/or centralized monitoring approach. Although such remote and/or centralized monitoring approaches can be effected for an individual subject (e.g., in a home hospice environment), such approaches are especially advantageous in connection with multi-subject care environments. For example, different sensor data from one subject or from several different subjects (in each case, such sensor data being locally generated and specifically associated with an intravenous fluid being administered to a particular subject) can be acquired and/or monitored at a location which is remote (relative to the patient)—such as a nursing station; preferably such sensor data can be centrally monitored at such remote location. In various aspects and embodiments therefore, sensor data can be generated in a processor local to and in communication with a sensor element (e.g., having a sensing element in contact with the intravenous fluid), preferably for each of two or more subjects, and then such locally-generated sensor data stream(s) can be acquired by a processor remote from the sensor element. Such acquisition can be effected, for example, via wireless (e.g., WiFi, Bluetooth®, WiMax, IR, RF) or other communication approaches. The remote processor can comprise one or more circuits for receiving, processing, storing, displaying or transmitting the acquired sensor data. The acquired sensor data can be monitored remotely, including for example at a central monitoring location. Preferably for example, the monitoring can be done visually by human interaction with a display and/or can be further enhanced and effected by various automated approaches. In one such automated monitoring approach, a monitoring circuit can comprise a data comparator module for comparing one or more parameters (e.g., data values) derived from sensor data with one or more parameters (e.g., data values) which are prescribed or proscribed for a particular subject (e.g. patient). Such patient-relevant parameters can be treatment-centric (e.g., applicable to all such patients undergoing a particular treatment), including semi-customized treatment-centric parameters which include a patient-specific data input (e.g., a patient weight, patient age, etc.) to determine a treatment-centric parameter, and/or such patient-relevant parameters can be patient-centric (e.g., wholly customized for a specific patient). Exemplary non-limiting parameters can include dosing levels, dosing timing (onset or completion), dosing frequency, etc. for various and specific active pharmaceutical agents or other components of an intravenous fluid. Patient-relevant parameters can be specific for the intravenous monitoring system affected by the apparatus, systems and methods of the invention, and/or can be common with (e.g., shared with) various other systems, such as infusion pump systems (e.g., "smart pumps"). In one embodiment, such infusion pump includes a control system with a data input module, whereby patient-specific data (e.g., weight) can be used to determine a patient relevant parameter used by both the pump controller (as known in the art) and/or for use by the monitoring circuit, e.g. a comparator module, of the present inventions for comparison to a sensor-data parameter. In some embodiments, the monitoring circuit can share common circuitry with (or have the same or similar functionality and/or software as) a portion of the pump controller circuit. Advantageously, the monitoring approaches of the apparatus, systems and methods of the invention can also include certain notice (e.g., alarm) features—to provide notice to a caregiver that a specific patient's intravenous fluid delivery system is operating incongruous with a prescribed or proscribed treatment, and/or can also include certain corrective action (e.g., system control) features—to make, preferably automated, a corrective action with the intravenous fluid delivery system. For example, upon determining an inconsistency between corresponding sensor-data-derived parameter and prescribed or proscribed patient-relevant parameter, an alarm can sound and/or a control circuit can activate a control element (e.g., an automated infusion valve) to make a change in the intravenous administration regime. Such remote and/or central monitoring approaches can further enhance the benefit to patient safety, by reducing the potential for errors associated with intravenous administration, and especially intravenous drug administration. The various remote and/or central monitoring approaches as described herein are preferred, an can be generally used with any aspects, embodiments and approaches described herein; however, many aspects, embodiments and approaches of the invention do not require such remote and/or central monitoring approaches and can be effected independently thereof.

Generally, and preferably, the apparatus, systems and methods of the invention are directed to or effective for identifying one or more components of an intravenous fluid during administration of the fluid to a subject with a sensor that comprises a processor (e.g., as included within a processor assembly) which is physically separable from, and intermittently interfaceable with (e.g., for a finite, operationally effective period of time) a sensor element (e.g., as included within a housing assembly). The approach of a temporally-limited engagement (interfacement) of the processor and the sensor element allows for regular operation while engaged/interfaced, and allows for physical separation of sensing function and processing function of a sensor (at least for some period of time) after or between operations, with a corresponding separation of physical treatment of the embodiments which effect such function. For example, the sensor element can be physically separated from the processor for a period of time to allow for sterilizing the sensor element (or a sensing surface thereof) or for disposal and replacement of a (pre-)sterilized sensor element (or a sensing surface thereof). Such separation also allows for re-use of the processor—for example, in connection with a second subsequent subject. Significantly, since processors are generally more expensive than sensor elements (or sensing surfaces thereof), the re-use of processors in such a temporally-limited engagement (interfacing) approach provides for efficiency of capital investment, especially in a multi-subject (e.g., hospital, surgical, nursing care, etc.) environment. The various approaches for temporally-limited/intermittent engagement/interfacing of processor and sensor element as described herein are preferred, an can be generally used with any aspects, embodiments and approaches described herein; however, many aspects, embodiments and approaches of the invention do not require such approaches for temporally-limited/intermittent engagement/interfacing of processor and sensor element, and can be effected independently thereof.

Generally, and preferably, the apparatus, systems and methods of the invention are directed to or effective for identifying one or more components of an intravenous fluid during administration of the fluid to a subject with a sensor that comprises (i) an assembly comprising one or more sensor elements, (ii) a signal-conditioning processor, including one or more circuits adapted for conditioning (e.g., amplifying) a signal, and (iii) a signal-identification processor, including one or more circuits adapted for identifying or determining a signal representative of the identity of one or more components of an intravenous fluid (e.g. as corresponding to a component within a composition or concentration of a component within a composition). In one such preferred subembodiment, each of the assembly comprising the one or more sensor elements, the signal-conditioning processor, and the signal-identification processor are each physically separate components. In an alternative of such preferred subembodiment, the assembly comprising the one or more sensor elements is physically separate from an integrated assembly comprising the signal-conditioning processor and the signal-identification processor. In another such preferred subembodiment, an integrated assembly comprises each of the one or more sensor elements, the signal-conditioning processor, and the signal-identification processor. Such various approaches for configuring the sensor elements, the signal-conditioning processor and the signal-identification processor are preferred, an can be generally used with any aspects, embodiments and approaches described herein; however, many aspects, embodiments and approaches of the invention do not require such approaches for configuring these sensor components, and can be effected independently thereof.

Various further aspects, embodiments and features of the inventions are described herein throughout the specification and drawings; the aforementioned general summary is intended to be an introductory and non-limiting summary of several commercially meaningful approaches included separately and in combination in various inventions. Generally, these various inventions enhance the accuracy and/or reliability of treatments involving intravenous administration, thereby reducing risk of error in connection with such treatments, and improving patient safety. The various inventions also enable improved effectiveness and efficiency of operations and improved efficiency of capital investment, especially in a multi-subject environment. The following more detailed summary, and the subsequent detailed description and examples further describe the inventions.

In particular, in a first aspect, the invention is directed to apparatus comprising a sensor (or a sensor subassembly) for identifying one or more components of an intravenous fluid. In general, in this first aspect of the invention the apparatus comprises one or more sensor elements having a sensing surface responsive to a fluid (e.g., to a fluid property or a fluid composition). Preferably, the sensing surface of a sensor element is positioned for contact with the intravenous fluid. Alternatively, however, the sensing surface of a sensor element can be positioned for indirect, non-contact sensing of a fluid. Preferably, the sensing surface of a sensor element is positioned for contact with the intravenous fluid during the administration of the fluid to the subject.

In a first general embodiment of the first aspect of the invention, the invention is directed to an apparatus effective for multi-parametric characterization of one or more fluid components. Preferably, in this first general embodiment, the apparatus comprises two or more sensor elements, each sensor element having a sensing surface positioned for contact with the fluid. Preferably, in this first general embodiments, the two or more sensor elements can have a surface positioned in one or more cavities of a housing. The housing can be adapted for fluidic interface with a fluid line assembly of an intravenous fluid delivery system. For example, the housing can be adapted for in-line fluid communication with the fluid line assembly. Alternatively, the housing can be defined or included in an intravenous infusion device (e.g., a catheter). The two or more sensor elements can be independent of each other, including for example having physically separate sensing surfaces, and/or for example having sensing surfaces which are independently addressable (e.g., independently activated, independently sampled, including for example simultaneously using differentially resolvable (deconvolutable) approaches or at different times). In preferred subembodiments of this first general embodiment, the apparatus can comprise one or more signal processing circuits for (preferably independently) processing data originating from each of the two or more sensor elements, the processing circuits being configured to generate a multi-parametric profile characteristic of a component of the fluid.

In a second general embodiment of the first aspect of the invention, the invention is directed to an apparatus effective for deploying sensor elements and sensor processors (e.g., including one or more circuits for activating a sensor element or for receiving, processing, storing, displaying or transmitting data originating from the sensor element) in a capital efficient manner. Preferably, in this second general embodiment, the apparatus comprises one or more sensor elements. The sensor element(s) can have a sensing surface positioned for contact with the fluid. Preferably, in this second general embodiment, the sensing surface can be positioned in one or more cavities of a housing. The housing can be adapted for fluidic interface with a fluid line assembly of an intravenous fluid delivery system. For example, the housing can be adapted for in-line fluid communication with the fluid line assembly. Alternatively, the housing can be defined or included in an intravenous infusion device (e.g., a catheter). In any case, the apparatus in this second embodiment, can further comprise one or more contacts in communication with (e.g., in electrical communication with) the sensing surface of the sensor element(s). Such contacts are preferably accessible, to enable a communication interface with a sensor processor. The sensor processor can be in a processor assembly which contains the one or more circuits (as described herein above). The processor assembly can further comprise one or more contacts in communication with the one or more circuits. Such contacts are preferably accessible, for intermittent communication interface with the contacts of the sensing surfaces. The intermittent interface of this general second embodiment of the first aspect of the invention allows for deployment of a relatively inexpensive housing assembly comprising the one or more sensor element(s), which housing assembly or sensor elements or sensing surfaces thereof can be sterile or sterilizable for use, and/or which can be disposable after use. Such housing assembly or sensor elements or sensing surfaces can be deployed in practice with a reusable sensor processor (e.g., as a processor assembly), thereby providing for capital efficiency. For example, a sensor processor can be interfaced with a first housing assembly for use by a first subject, and following thereafter, the same sensor processor can be interfaced with a second housing assembly for use by a second subject. Further related methods and aspects are described below.

In a third general embodiment of the first aspect of the invention, the invention is directed to an apparatus effective for ensuring and enhancing the reliability and/or accuracy of a patient-specific treatment. Preferably, in this third general embodiment the apparatus comprises one or more sensor elements. The sensor element(s) can have a sensing surface positioned for contact with the fluid. Preferably, the sensing surface can be positioned in one or more cavities of a housing, as described above in connection with the second general embodiment of the first aspect of the invention. The apparatus can comprise a sensor processor. The sensor processor can include one or more circuits for activating a sensor element or for receiving, processing, storing, displaying or transmitting data originating from the sensor element. Preferably, the apparatus can comprise one or more of a signal processing circuit and/or a data retrieval circuit. Preferably, the apparatus can further comprise an identifier circuit for correlating sensor data to a specific patient. The identifier circuit is preferably in communication with (e.g., electrical communication with) one or more of a signal processing circuit and/or a data retrieval circuit. The identifier circuit can be used in operation to effectively monitor whether a specific patient is receiving an intravenous fluid consistent with a prescribed or proscribed treatment plan.

In a fourth general embodiment of the first aspect of the invention, the invention is directed to an apparatus effective for deploying a fluid-component sensor into in intravenous delivery system. Preferably, in this fourth general embodiment of the first aspect of the invention, the apparatus comprises an infusion device for infusion of fluid into the vasculature system of a subject, and one or more sensor elements integral with the infusion device. The sensor element(s) can have a sensing surface positioned for contact with the fluid. Preferably, the sensing surface can be positioned in one or more cavities (e.g., of a housing) defined in the infusion device.

The first, second, third and fourth general embodiments of the first aspect of the invention can be effected in combination with each other. The first, second, third and fourth general embodiments of the first aspect of the invention can be effected and/or used as well with each general embodiment of the second and third aspects of the invention. Various specific subembodiments of each general embodiments of the first aspect of the invention are also applicable with specific subembodiments of general embodiments of the second and third aspects of the invention.

In a second aspect, the invention is directed to systems for intravenous delivery of fluids into a subject in need thereof (e.g., a patient). In general, in this second aspect of the invention the system comprises a fluid line assembly and one or more sensor elements. The fluid line assembly can generally include one or more conduits and/or other components. The fluid line assembly can have a first end adapted for fluid communication with a fluid source and a second distal end adapted for fluid communication with an intravenous infusion device for infusion of fluid into the vascular system of the subject (e.g., a patient). The sensor element(s) can have a sensing surface positioned for contact with the fluid. Preferably, in this first general embodiment of the second aspect of the invention, the sensing surface can be positioned in one or more cavities of a housing. The housing can be adapted for fluidic interface with a fluid line assembly of an intravenous fluid delivery system. For example, the housing can be adapted for in-line fluid communication with the fluid line assembly. Alternatively, the housing can be defined or included in an intravenous infusion device (e.g., a catheter).

In a first general embodiment of the second aspect of the invention, the invention is directed to a system for intravenous fluid delivery to a patient comprising a fluid line assembly and an apparatus of the first aspect of the invention.

In a second general embodiment of the second aspect of the invention, the invention is directed to a system for intravenous fluid delivery to a patient comprising a fluid line assembly having a first end adapted for fluid communication with a fluid source and a second distal end adapted for fluid communication with an intravenous infusion device for infusion of fluid into the vascular system of the subject (e.g., a patient). The system further comprises a sensor element having a sensing surface proximate to the second distal end of the fluid line assembly. The sensing surface can be positioned in one or more cavities of a housing. The housing can be adapted for fluidic interface with a fluid line assembly proximate to its distal end. For example, the housing can be adapted for in-line fluid communication with the fluid line assembly proximate to its distal end. Alternatively, the housing can be defined or included in an intravenous infusion device (e.g., a cannula or a catheter). The system can further comprise one or more injection ports and one or more additional sensor elements for one or more additional sensors, such additional sensor elements being positioned upstream of the injection port—facilitating for example a differential measurement approach.

In a third general embodiment of the second aspect of the invention, the invention is directed to a system for intravenous fluid delivery to a subject which includes a remote processor, effective for example for monitoring sensor data from one or from multiple local sensors (e.g., for remote monitoring of a corresponding multiple subjects). The remote processor can therefore comprise a data acquisition circuit for acquiring sensor data originating from one or more local sensors (e.g., via a corresponding one or more local processors), and a monitoring circuit for monitoring the sensor data. The system can include a local processor comprising one or more circuits for activating a sensor element or for receiving, processing, storing, displaying or transmitting data originating from the sensor element. Preferably, the apparatus can comprise one or more of a signal processing circuit and/or a data retrieval circuit. Preferably, the system can further comprise an identifier circuit for correlating sensor data to a specific patient. The local processor can be proximate to and in communication with one or more sensing surfaces of a sensor element. The sensor element can have a sensing surface positioned to contact the fluid during administration to the subject, as described.

In a further, fourth general embodiment of the second aspect of the invention, the invention is directed to a system for intravenous fluid delivery to a subject comprising a fluid line assembly and a sensor for identifying one or more active pharmaceutical agents within the fluid. The sensor can comprise a sensor element having a sensing surface positioned for contact with the fluid, and one or more circuits in communication with the sensor element for activating the sensor element or for receiving, processing, storing, displaying or transmitting data originating from the sensor element. The sensor is configured to distinguishably detect one or more active pharmaceutical agents. Preferably, the sensor is configured to identify one or more active pharmaceutical agents selected from the group consisting of an anticoagulant (e.g., heparin), a metabolically-active hormone (e.g., insulin), an anesthetic (e.g., propofol), and an analgesic (e.g., morphine).

In another, fifth general embodiment of the second aspect of the invention, the invention is directed to a system for intravenous fluid delivery to a subject comprising a fluid line assembly and a sensor for identifying one or more components of the fluid. The sensor can comprise a sensor element having a sensing surface positioned for contact with the fluid, and one or more circuits in communication with the sensor element for activating the sensor element or for receiving, processing, storing, displaying or transmitting data originating from the sensor element. The sensor is configured to distinguishably detect one or more components of the fluid. Preferably, the sensor is configured to identify one or more components of the fluid selected from the group consisting of a metal ion, halide ion, organic ion or salts, and a sugar, preferably for example sodium ion, potassium ion, chloride ion, calcium ion, magnesium ion, lactate ion, and dextrose. For example, such ions can be components in fluid compositions comprising potassium chloride, sodium chloride, Ringer's lactate, and dextrose. Preferably, the method comprises sensing the fluid to identify potassium chloride, potassium ion or chloride ion.

In a sixth general embodiment of the second aspect of the invention, the invention is directed to a system for intravenous fluid delivery to a subject comprising a fluid line assembly and a sensor other than a flow sensor, the sensor comprising a sensor element having a sensing surface positioned for contact with the fluid. The sensor can preferably further comprise one or more circuits in communication with the sensor element for activating the sensor element or for receiving, processing, storing, displaying or transmitting data originating from the sensor element.

The first, second, third, fourth, fifth and sixth general embodiments of the second aspect of the invention can be effected in combination with each other. The first, second, third, fourth, fifth and sixth general embodiments of the second aspect of the invention can be effected and/or used as well with each general embodiment of the first and third aspects of the invention. Various specific subembodiments of each general embodiments of the second aspect of the invention are also applicable with specific subembodiments of general embodiments of the first and third aspects of the invention.

In a third aspect, the invention is directed to methods for intravenous delivery of fluid to a subject in need thereof (e.g., a patient). In general, such methods comprise administering an intravenous fluid to a subject in need thereof and sensing the fluid, preferably to identify one or more components thereof.

In a first general embodiment of the third aspect of the invention, the invention is directed to a method for intravenous delivery of fluid to a subject in need thereof. The method comprises administering the fluid to the subject, and sensing the fluid with an apparatus of the first aspect of the invention or with a system of the second aspect of the invention. Preferably, the method further comprises identifying one or more components of the fluid during administration of fluid to the subject.

In a second general embodiment of the third aspect of the invention, the invention is directed to a method for intravenous delivery of fluid to a subject in need thereof. The method comprises administering the fluid to the subject, sensing the fluid to generate a multi-parametric profile characteristic of a component of the fluid, and identifying one or more components of the fluid during administration of fluid to the subject based on the multi-parametric profile. In preferred subembodiments, sensing the fluid comprises exposing a sensing surface of a first sensor element to the fluid, exposing a sensing surface of a second sensor element to the fluid, and independently processing data originating from each of the first sensor element and the second sensor element to generate the multi-parametric profile.

In a third general embodiment of the third aspect of the invention, the invention is directed to a method for intravenous delivery of fluid to a subject in need thereof. The method comprises administering a first fluid to a first subject, exposing a sensing surface of a first sensor element to the first fluid, interfacing (e.g., communicatively engaging) a processor with the first sensor element and identifying one or more components of the first fluid during administration thereof to the first subject. The processor can comprise one or more circuits for activating a sensor element or for receiving, processing, storing, displaying or transmitting data originating from the a sensor element. The method further comprises dis-interfacing (e.g., communicatingly disengaging) the processor from the first sensor element. The method further comprises administering a second fluid to a second subject, exposing a sensing surface of a second sensor element to the second fluid, and interfacing the (same) processor with the second sensor element and identifying one or more components of the second fluid during administration thereof to the second subject. This method preferably, in a subembodiment, can further comprise disposing or sterilizing the sensing surface of each of the first sensor element and the second sensor element after administration of fluid to the respective subject.

In a fourth general embodiment of the third aspect of the invention, the invention is directed to a method for intravenous delivery of fluid to a subject in need thereof. The method comprises administering the fluid to the subject, sensing the fluid to generate sensor data for identifying one or more components of the fluid during administration of fluid to the subject, and correlating the sensor data to the specific subject. Preferably, this method can further comprise deriving one or more parameters from the sensor data, and comparing the one or more sensor-derived parameters with one or more prescribed or proscribed patient-relevant parameters.

In a fifth general embodiment of the third aspect of the invention, the invention is directed to a method for intravenous delivery of fluid to a subject in need thereof. The method comprises administering the fluid to the subject through an intravenous infusion device, and sensing the fluid with a sensing surface of a sensor element, where the sensing surface is positioned proximate to the intravenous infusion device to identify one or more components of the fluid during administration of fluid to the subject. Preferably in this method, fluid is exposed to a sensing surface of a sensor element, with the sensing surface being positioned within a cavity of a housing adapted for in-line fluid communication of a fluid line assembly. Preferably in this method, such an in-line housing is positioned directionally adjacent to the subject relative to the position of any fluid source supply line or any injection port of the fluid line assembly. Alternatively for this method, fluid is exposed to a sensing surface of a sensor element, and the sensing surface being positioned within a cavity of a housing defined in the intravenous infusion device.

In a sixth general embodiment of the third aspect of the invention, the invention is directed to a method for intravenous delivery of fluid to a subject in need thereof. The method comprises administering the fluid to the subject, sensing the fluid with a sensor element having a sensing surface exposed to the fluid during administration of fluid to the subject, generating sensor data in a processor local to and in communication with the sensor element, the local processor optionally comprising one or more circuits for activating a sensor element, the local processor comprising one or more circuits for receiving, processing, storing, displaying or transmitting data originating from the sensor element. The method further comprises acquiring the sensor data at a processor remote from the sensor element. The remote processor can comprise one or more circuits for receiving, processing, storing, displaying or transmitting the acquired sensor data. The method further comprises monitoring the acquired sensor data or data derived therefrom.

In a seventh general embodiment of the third aspect of the invention, the invention is directed to a method for intravenous delivery of fluid to two or more subjects in need thereof. The method comprises administering a first fluid to a first subject, sensing the first fluid with a first sensor element having a sensing surface exposed to the first fluid during administration of fluid to the first subject, and generating sensor data in a first processor local to and in communication with the first sensor element. The method further comprises administering a second fluid to a second subject, sensing the second fluid with a second sensor element having a sensing surface exposed to the second fluid during administration of fluid to the second subject, and generating sensor data in a second processor local to and in communication with the second sensor element. The method can further include acquiring the sensor data from each of the first local processor and the second local processor at a processor remote from each of the first sensor element and the second sensor element, and monitoring the acquired sensor data from each of the first local processor and the second local processor or monitoring data derived therefrom.

In an eighth general embodiment of the third aspect of the invention, the invention is directed to a method for intravenous delivery of fluid to two or more subjects in need thereof. The method comprises administering the fluid to the subject, and sensing the fluid to identify one or more active pharmaceutical agents within fluid during administration of fluid to the subject. Preferably, the method of this eighth general embodiment comprises sensing the fluid to identify one or more active pharmaceutical agents selected from the group consisting of: an anticoagulant (e.g., heparin), a metabolically-active hormone (e.g., insulin), an anesthetic (e.g., propofol), and an analgesic (e.g., morphine).

In a ninth general embodiment of the third aspect of the invention, the invention is directed to a method for intravenous delivery of fluid to two or more subjects in need thereof. The method comprises administering the fluid to the subject, sensing the fluid to identify one or more components within fluid during administration of fluid to the subject, the one or more components being selected from the group consisting of a metal ion, halide ion, organic ion or salts, and a sugar, preferably for example sodium ion, potassium ion, chloride ion, calcium ion, magnesium ion, lactate ion, and dextrose. For example, such ions can be components in fluid compositions comprising potassium chloride, sodium chloride, Ringer's lactate, and dextrose. Preferably, the method comprises sensing the fluid to identify potassium chloride, potassium ion or chloride ion.

The first, second, third, fourth, fifth, sixth, seventh, eighth and ninth general embodiments of the third aspect of the invention can be effected in combination with each other. The first, second, third, fourth, fifth, sixth, seventh, eighth and ninth general embodiments of the third aspect of the invention can be effected and/or used as well with each general embodiment of the first and second aspects of the invention. Various specific subembodiments of each general embodiments of the third aspect of the invention are also applicable with specific subembodiments of general embodiments of the first and second aspects of the invention.

Various embodiments of the invention as described above and hereinafter include listings of groups of alternatives (e.g., Markush groups); in each case, any such listing is intended to disclose each such member of the group collectively as well as individually.

Various features of the invention, including features defining each of the various aspects of the invention, including general and preferred embodiments thereof, can be used in various combinations and permutations with other features of the invention. Features and advantages are described herein, and will be apparent from the drawings and the following detailed description.

BRIEF DESCRIPTION OF THE DRAWINGS

FIG. 4 illustrates a schematic representation of a multiparametric approach for identifying one or more components of the intravenous fluid.

Figure 1A:
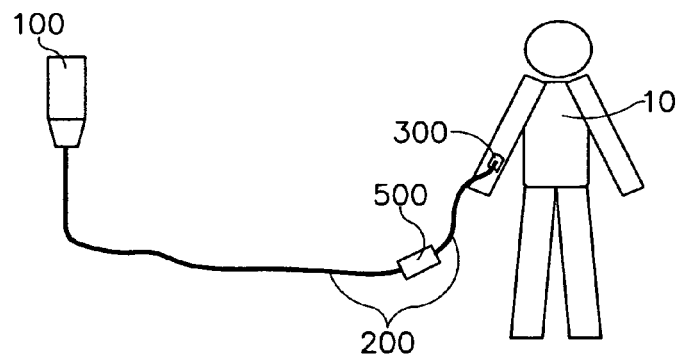
FIG. 1(A-C) illustrate schematic representations of intravenous fluid delivery systems, including a contextual schematic illustration showing general features (FIG. 1A), and more detailed schematic illustrations showing further features thereof (FIG. 1B, FIG. 1C).

Various aspects of the figures are described in further detail below, in connection with the detailed description.

DETAILED DESCRIPTION OF THE INVENTION

The present inventions provide apparatus, systems and methods related to intravenous fluid administration. The apparatus, systems and methods of the invention are more specifically related to monitoring of intravenous fluids during administration to a subject.

Generally, as summarized above and described in further detail below, the apparatus, systems and methods of the invention are directed to or effective for identifying one or more components of an intravenous fluid during administration of the fluid to a subject. Preferably, the apparatus, systems and methods of the invention are directed to or effective for identifying one or more active pharmaceutical agents within an intravenous fluid during administration of the fluid to a subject. Other components can also be detected, especially components relevant to hydration and/or ion metastasis (e.g., electrolyte balance) and/or vasculature pressure of patients. The one or more components of an intravenous fluid can preferably be identified during administration of the fluid to a subject using a multi-parametric approach. Many specific sensors known in the art can be used in connection with the various aspects and embodiments of the invention. Preferred sensors include one or more sensors selected from an impedance sensor (e.g., an AC impedance spectroscopy sensor), an electrochemical sensor (e.g., an electrochemical potential sensor), a thermal sensor (e.g., a thermal anemometer sensor), an optical sensor (e.g., a refractometry sensor, a transmission sensor, an absorbance sensor, a spectrometer (including a colorimeter), a turbidity sensor), a Theological sensor (e.g., a viscometer), an electrical property sensor (e.g., a capacitor sensor, a pH sensor, a conductivity sensor, and an inductive sensor), and a fluid-displacing or fluid-shearing (e.g., resonator) sensor. Preferably, a system comprises two or more sensors, for example an integrated assembly comprising two or more sensor elements, each comprising one or more sensing surfaces (e.g., an impedance sensor and an optical (e.g., refractive index) sensor). Preferably, a sensor having a sensor element (e.g., with a sensing surface adapted for interaction with and being responsive to the intravenous fluid) is positioned such that the sensor element (e.g., the sensing surface) within an intravenous fluid system such that it interacts with the fluid (e.g., such sensing surface contacts the fluid) in relative proximity to the infusion location—the location at which the fluid enters a subject's vasculature system, e.g., proximal to the distal end of the fluid line assembly or proximal to the intravenous infusion device. Preferably, the apparatus, systems and method of the invention provide for the subject being positively and specifically identified in connection with monitoring and administration of the intravenous fluid; hence, for example, the sensor (or apparatus or system comprising a sensor) can include an identifier circuit for correlating sensor data to a specific subject. Preferably, the systems are effected with a remote and/or centralized monitoring approach. For example, different sensor data from one subject or from several different subjects (in each case, such sensor data being locally generated and specifically associated with an intravenous fluid being administered to a particular subject) can be acquired and/or monitored at a location which is remote (relative to the patient)—such as a nursing station; preferably such sensor data can be centrally monitored at such remote location. For example and without limitation, monitoring can be visual by human interaction with a display and/or can be further enhanced and effected by various automated approaches, including automated approaches involving notice to caregivers (alarms, emails, text message) and/or specific corrective or subsequently prescribed actions within the system. In preferred embodiments of various aspects of the invention, the sensor can comprise a processor which is physically separable from, and conversely, intermittently interfaceable with a sensor element. Such temporally-limited engagement (interfacement) of processor and sensor element allows for an operational period (while engaged/interfaced) and a non-operational period (with physical separation of sensor element from the processor). The non-operational period can allow for sterilizing the sensor element (or a sensing surface thereof) or for disposal and replacement of a (pre-)sterilized sensor element (or a sensing surface thereof). The processor can be re-used, for example, in connection with a second subject, either in the same location (a later subject) or in a different location (e.g., multiplexing the same processor over various subjects). In preferred embodiments of various aspects of the invention, the sensor can comprise: an assembly comprising one or more sensor elements; a signal-conditioning processor, including one or more circuits adapted for conditioning (e.g., amplifying) a signal; and a signal-identification processor, including one or more circuits adapted for identifying or determining a signal representative of the identity of one or more components of an intravenous fluid. The various aforementioned attributes and features of the inventions can be used in each of the various possible combinations and permutations with each other, as applicable.

As described herein and in further detail below, the various inventions offer intravenous fluid monitoring approaches which are significantly advantaged over known systems, including for example by providing near real-time monitoring of the identity of one or more components of an intravenous fluid (e.g., the presence or absence of a component, the composition of a component, the concentration of a component, the time of infusion (absolute time or relative time versus other components), the onset of component delivery; the completion of component infusion, the cumulative dosing level (e.g., current or projected) of a component being delivered, etc.). Such near real-time monitoring of intravenous fluids reduces the potential for errors associated with intravenous administration, and especially intravenous drug administration. Hence, the apparatus, systems and methods of the invention provide substantial advances in patient safety. Such advances in safety can translate to a more meaningful patient treatment experience, and to enhanced operational efficiencies and reduced expenses for hospitals and other entities which administer fluids intravenously. Such inventions can applied, and such advantages can be realized in a number of various settings and applications in which intravenous fluids are administered, including for example, without limitation, at hospitals, clinics, surgical centers, homes (e.g., home hospice), nursing homes, assisted living environments, etc.

Intravenous Fluid Delivery Systems

Figure 1B:
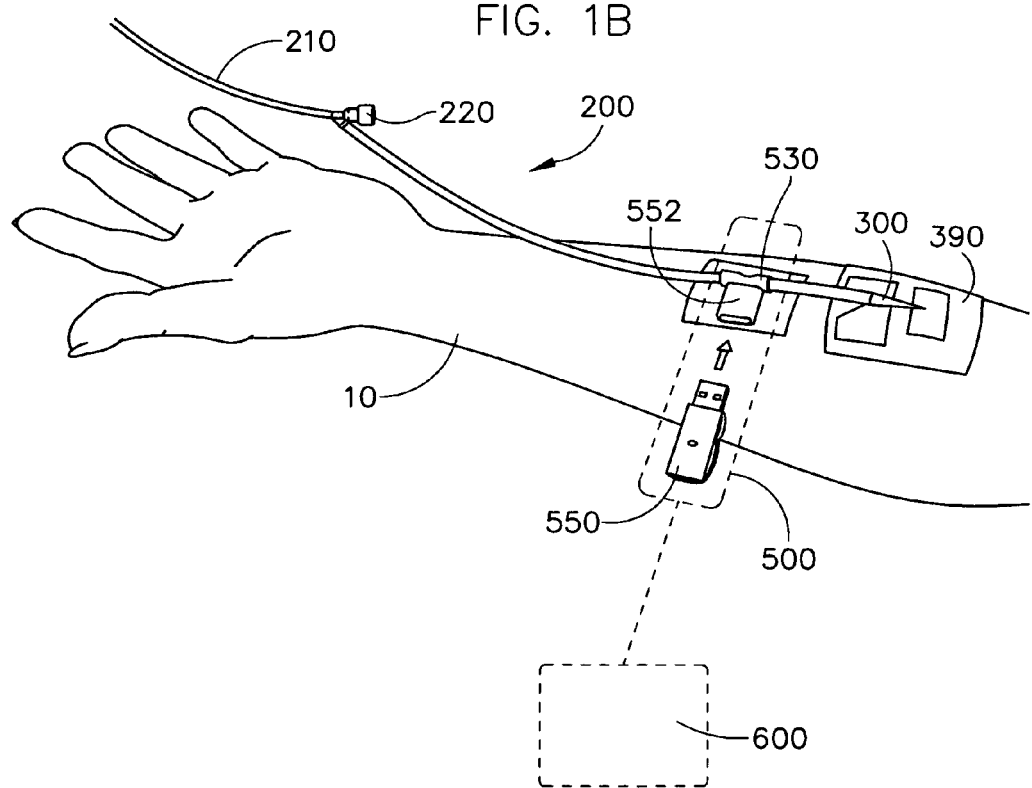
Figure 1C:
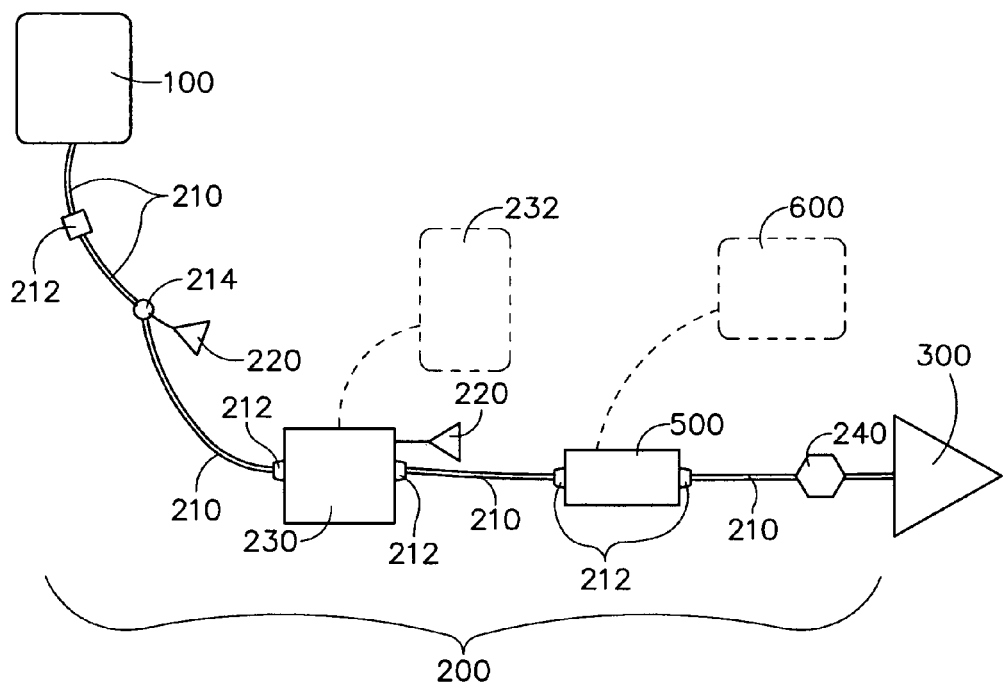
Figure 2:
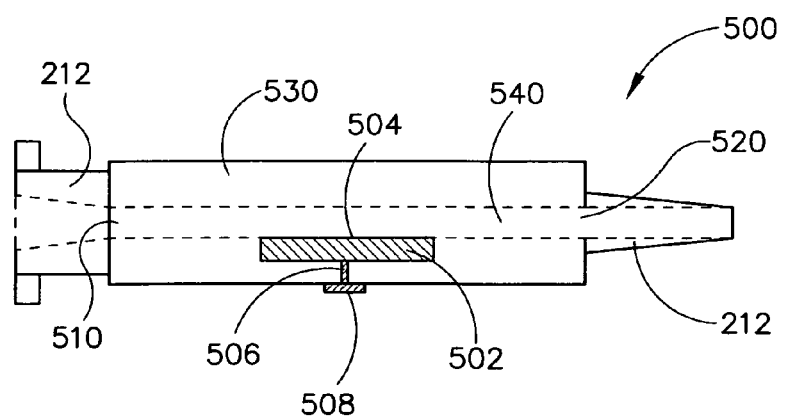
FIG. 2 illustrates a schematic representation of an embodiment of an apparatus comprising a sensor element having a sensing surface integrated into an in-line housing adapted for fluidic interface with a fluid line assembly.
Figure 3A:
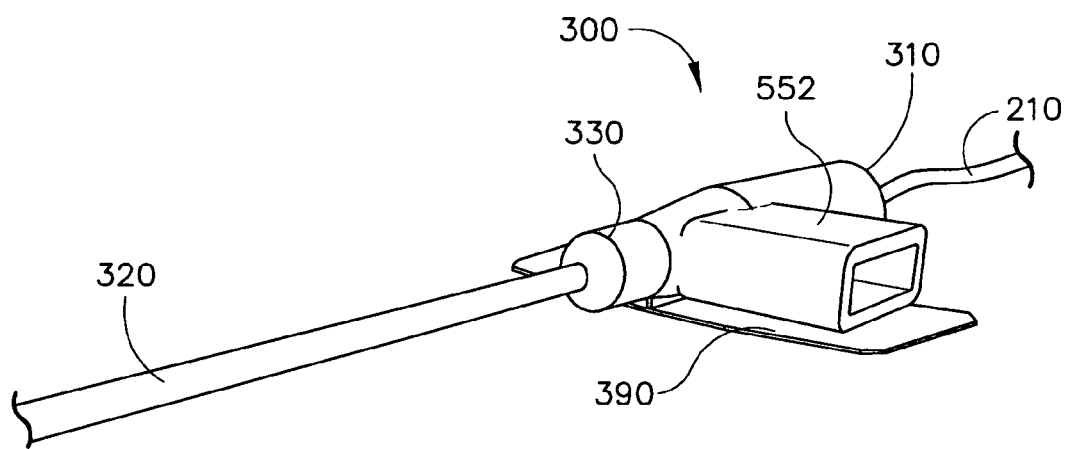
FIG. 3(A-C) illustrate schematic representations of an embodiment of an apparatus comprising a sensor element having a sensing surface integrated into an intravenous infusion device (e.g., catheter) adapted for fluid communication with fluid line assembly, including a perspective view (FIG. 3A), side cut-away elevation (FIG. 3B), and detail of the sensor element containing portion thereof (FIG. 3C).

Generally, an intravenous fluid delivery system of the invention can include various systems known in the art or later developed which provide for delivery of fluids to the vasculature system of a subject in need thereof. Generally, such systems can be intermittent or continuous (e.g., including intravenous drip systems). With reference to FIGS. 1A through 1C, in operation intravenous fluid delivery systems generally comprise an intravenous fluid source 100 in fluid communication with an intravenous infusion device 300 through a fluid line assembly 200. The intravenous infusion device 300 is adapted for infusion of fluid into the vasculature system (e.g., a vein) of a subject 10. With further reference to FIG. 2 and FIGS. 3A through 3C, the intravenous fluid delivery systems of the invention can comprise a sensor 500 comprising one or more sensor elements 502 having a sensing surface 504. The sensing surface 504 can be in communication (e.g., electrical communication via electrical connector 506) to one or more contacts 508).

Various intravenous fluid delivery system configurations can be employed, and various such intravenous infusion devices can be employed. For example, the intravenous fluid delivery system can be configured for peripheral intravenous infusion, for central intravenous infusion, or for peripherally-inserted central intravenous infusion. The system can be adapted for various infusion profiles and approaches; for example, infusion can be rapid, can be drip, can be continuous or can be intermittent.

Various suitable intravenous infusion device can be used in connection with the invention. Preferably, as shown in the FIGS. 1A through 1C, such intravenous infusion devices 300 can be integrated with or in fluid communication with a fluid line assembly 200 and/or a fluid source 100. Generally, and with reference to FIGS. 3A through 3C, such an intravenous infusion device 300 (e.g., a catheter) can comprise a first end 310 adapted for fluid communication with a fluid line assembly, a second distal end 320 adapted for insertion through the skin into the vasculature system of the subject, preferably through a peripheral vein, and a housing 330 (e.g., a catheter hub), providing excorporal structural support and having a cavity 340 providing fluid communication between the first end 310 and the second distal end 320 of the infusion device. The intravenous infusion device 300 can also include a support element 390 (e.g., such as adhesive wings) for supporting the device 300 during administration of fluid to a subject. Other intravenous infusion devices can also be used in connection with aspects and embodiments of the inventions. Such devices can include for example an integrated fluid source—for example, a needle-type infusion device (e.g., comprising a syringe a needle in fluid communication with the syringe). Such devices can also include ported cannulae having an injection port on a first end and a second distal end adapted for insertion through the skin into the vasculature system of the subject. The intravenous infusion device can also include an implantable infusion device such as an implantable port. The port can be, for example, a central venous line comprising a cavity covered with a pliable sealant as a cavity cover (e.g., silicone rubber) and adapted for being implanted under the skin. A fluid can be administered through such implantable port intermittently by placing a small needle or catheter through the skin, piercing the silicone, and administering the fluid into the cavity. The cavity cover can reseal after withdrawal of the needle or catheter.

Other system components can include, for example in a typical intravenous fluid delivery system, one or more sterile containers (glass bottle, plastic bottle or plastic bag) adapted for containing (or pre-filled to contain) fluids, typically configured with an attached drip chamber. The system can comprise a fluid line assembly comprising one or more conduit sections (e.g., each conduit for example comprising a long sterile tube), optionally configured with a clamp to regulate or stop the flow, various connectors, one or more infusion pumps, adapted for providing control over the flow rate and total amount of fluid delivered.

Pharmaceutical Agents, Other Components and Preferred Sensors

Generally, the apparatus, systems and methods of the invention are directed to or effective for identifying one or more components of an intravenous fluid during administration of the fluid to a subject. The intravenous fluid is not narrowly critical and can be of various types, including generally for example crystalloid solutions and colloid solutions. Crystalloid solutions can comprise aqueous solutions of mineral salts or other water-soluble molecules, including active pharmaceutical agents. Colloids can comprise larger semi-soluble or insoluble molecules, including active pharmaceutical agents. Generally, the intravenous fluids are sterile fluids.

Preferably, the apparatus, systems and methods of the invention are directed to or effective for identifying one or more active pharmaceutical agents within an intravenous fluid during administration of the fluid to a subject. Such active pharmaceutical agents can include, for example, an anticoagulant (e.g., heparin), a metabolically-active hormone (e.g., insulin), an anesthetic (e.g., propofol), and/or an analgesic (e.g., morphine), among others. Various one or more sensors are configured for sensing a property of a fluid which can be correlated to identify an active pharmaceutical agent component of the fluid. For example, the sensor can comprise one or more sensor elements having a sensing surface positioned for contact with the fluid, and one or more circuits in communication with the sensor element for activating the sensor element or for receiving, processing, storing, displaying or transmitting data originating from the sensor element. The sensor can be configured to distinguishably detect one or more active pharmaceutical agents. Preferably, the sensor is configured to identify one or more active pharmaceutical agents selected from the group consisting of an anticoagulant (e.g., heparin), a metabolically-active hormone (e.g., insulin), an anesthetic (e.g., propofol), and an analgesic (e.g., morphine).

Additionally or alternatively, the apparatus, systems and methods of the invention are directed to or effective for identifying one or more other components of an intravenous fluid, preferably components used for hydration and ion metastasis of subjects. Such components can preferably include, for example one or more components selected from potassium chloride, sodium chloride, Ringer's lactate, and dextrose, in each case in molecular or ionic (e.g., dissociated) form (e.g., sodium ion, potassium ion, chloride ion, calcium ion, lactate ion, and dextrose). The sensor can comprise a sensor element having a sensing surface positioned for contact with the fluid, and one or more circuits in communication with the sensor element for activating the sensor element or for receiving, processing, storing, displaying or transmitting data originating from the sensor element. The sensor can be configured to distinguishably detect one or more components of the fluid. Preferably, the sensor is configured to identify one or more components of the fluid selected from the group consisting of a metal ion, halide ion, organic ion or salts, and a sugar, preferably for example sodium ion, potassium ion, chloride ion, calcium ion, magnesium ion, lactate ion, and dextrose. For example, such ions can be components in fluid compositions comprising potassium chloride, sodium chloride, Ringer's lactate, and dextrose. Preferably, the method comprises sensing the fluid to identify potassium chloride, potassium ion or chloride ion.

Typical intravenous fluids can comprise normal saline, preferably for example a solution of sodium chloride at 0.9% concentration, which is close to the concentration in the blood (isotonic). The intravenous fluid can comprise Ringer's lactate or Ringer's acetate, another isotonic solution. In some instances, the intravenous fluid can comprise a sugar such as dextrose, for example a solution of 5% dextrose in water, sometimes referred to as D5W. The selection of a particular carrier fluid may also depend on the chemical properties of the active pharmaceutical agents being administered.

Table I shows compositions of common intravenous fluids used in connection with intravenous fluid delivery systems.

TABLE I

Composition of Intravenous Fluid Solutions

| Solution | Other Name | [Na+] (mmol/L) | [Cl] (mmol/L) | [Glucose] (mmol/L) | [Glucose] (mg/dl) |
|---|---|---|---|---|---|
| DW5 | 5% Dextrose | 0 | 0 | 278 | 5000 |
| ⅔D & ⅓S | 3.3% Dextrose/ 0.3% saline | 51 | 51 | 185 | 3333 |
| Half-normal saline | 0.45% NaCl | 77 | 77 | 0 | 0 |
| Normal saline | 0.9% NaCl | 154 | 154 | 0 | 0 |
| Ringer's lactate | Lactated Ringer | 130 | 109 | 0 | 0 |

Ringer's lactate also typically can have, for example and without limitation 28 mmol/L lactate, 4 mmol/L K+ and 3 mmol/L Ca2+.

Generally, and preferably, the apparatus, systems and methods of the invention are directed to or effective for identifying one or more components of an intravenous fluid during administration of the fluid to a subject using one or more sensors. The one or more sensors are preferably selected to include at least one sensor other than a flow sensor, and/or in some embodiments also preferably other than a pressure sensor, and/or in some embodiments also preferably other than an ultrasonic sensor. Generally for example, preferred sensors effective with the apparatus, systems and methods of the invention can include, without limitation, one or more sensors selected from an impedance sensor (e.g., an AC impedance spectroscopy sensor), an electrochemical sensor (e.g., an electrochemical potential sensor), a thermal sensor (e.g., a thermal anemometer sensor), an optical sensor (e.g., a refractometry sensor, a transmission sensor, an absorbance sensor, a spectrometer (including a colorimeter)r, a turbidity sensor), a Theological sensor (e.g., a viscometer), an electrical property sensor (e.g., a capacitor sensor, a pH sensor, a conductivity sensor, and an inductive sensor), and a fluid-displacing (e.g., resonator) sensor. The various specific sensors and sensing approaches as described herein are preferred, an can be generally used with any aspects, embodiments and approaches described herein; however, many aspects, embodiments and approaches of the invention do not require such certain specific sensors or sensing techniques and can be effected independently thereof.

Generally, the sensor can be adapted for identifying an anticoagulant, preferably heparin. Preferably the sensor is adapted for determining one or more properties of the fluid selected from electrochemical potential, impedance, refractive index and ultraviolet absorption, and for identifying an anticoagulant, preferably heparin, based on the one or more determined properties.

Generally, the sensor can be adapted for identifying a metabolically-active hormone, preferably insulin. Preferably, the sensor is adapted for determining one or more properties of the fluid selected from electrochemical potential, impedance, refractive index and visible absorption (color), and for identifying a metabolically-active hormone, preferably insulin, based on the one or more determined properties.

Generally, the sensor can be adapted for identifying an anesthetic, preferably propofol. Preferably, the sensor is adapted for determining one or more properties of the fluid selected from electrochemical potential, impedance, refractive index and visible absorption (color), and for identifying an anesthetic, preferably propofol, based on the one or more determined properties.

Generally, the sensor can be adapted for identifying an analgesic, preferably morphine. In some variations, the sensor is adapted for determining one or more properties of the fluid selected from electrochemical potential, impedance, refractive index and ultraviolet absorption, and for identifying an analgesic, preferably morphine, based on the one or more determined properties.

Generally, the sensor can be adapted for identifying one or more components selected from the group consisting of a metal ion, a halide ion, an organic ion or salt, and a sugar.

Generally, the sensor can be adapted for identifying potassium chloride, potassium ion or chloride ion. Preferably, the sensor is adapted for determining one or more properties of the fluid selected from electrochemical potential, impedance, refractive index and ultraviolet absorption, and for identifying potassium chloride, potassium ion or chloride ion based on the one or more determined properties.

Generally, in each of the above preferred embodiments, the sensor can be adapted for determining two or more properties of the fluid, and for identifying the one or more active pharmaceutical agents based on the two or more determined properties.

Preferred sensors and fluid properties for sensing various active pharmaceutical agents (e.g. drug formulations) and other components are shown in Table 2.

TABLE 2

Preferred Fluid Properties and Sensors for Various Fluid Components

| Fluid Property | Sensor Approach | Example Reference |
| --- | --- | --- |
| Complex conductivity or admittance | AC impedance spectroscopy | (1) |
| Ionic properties | Electrochemical potential | (2) |
| Thermal properties | Pulsed thermal anemometry, | (3) |
| Index of refraction | Refractometer, fiber optic refractometer | (4) |
| Optical absorption | Optical absorption spectrometry | (5) |
| Color | Spectrometer, colorimeter | (6) |
| Viscosity | Viscometer, resonator | (7) |
| Density | Viscometer, resonator | (8) |
| Dielectric constant | Capacitor, resonator | (9) |
| Turbidity | Turbidity sensor | (10) |
| Permeability | Chemical sensors with selective membranes | (11) |
| Ph | Ph meter, MEMS Ph sensor, chemical color change sensor, litmus (e.g., paper) | (12) |
| Conductivity | DC and or AC conductance | (13) |
| Air bubbles | Optical | (14) |
| Surface plasmon effects | Surface Plasmon sensor | (15) |
| Thermal lensing | Optical detection of refractive index change | (16) |
| Sono-luminescence spectroscopy | Colorimetric and spectral detection of species | (17) |
| Flow rate | Thermal anemometer, Doppler flow meter | (18) |

Generally, such sensor approaches and fluid-property measurements as shown in Table 2 can be effective for identification of one or more active pharmaceutical agents, or an intravenous solution component (e.g., saline, potassium chloride, dextrose, etc), in each case within an intravenous fluid during administration of the fluid to a subject. Chemical sensors with selective membranes can differentiate fluid permeability and be useful for example for identifying specific compounds selectively (e.g., based on selection of a particular membrane). Optical detection of air bubbles, can be effective for example for preventing an air embolism, and additionally or alternatively, for detecting flow system failures (and thereby helping to maintain flow). Measurement of flow rate by thermal anemometer and/or by Doppler flow meter can be effective, for example, for detecting blockages, controlling flow rate, determining dosing and detecting flow system failures (and thereby helping to maintain flow).

Without limitation, and without being bound by theory not expressly recited in the claims, the following references are representative examples of the sensor approach and/or the fluid property measurement as shown in Table 2:

(1) Impedance based flow sensors Green, N. G., Tao, S., Holmes, D. and Morgan, H. (2005) Impedance based flow sensors. In: Microtechnologies for the New Millennium 2005 SPIE, 9-11 May 2005.
(2) http://www.resonancepub.com/electrochem.htm
(3) A pulsed-wire technique for velocity and temperature measurements in natural convection flows; Journal Experiments in Fluids; Publisher: Springer Berlin/Heidelberg; ISSN 0723-4864 (Print) 1432-1114 (Online) Issue Volume 18, Numbers 1-2/December, 1994
(4) Refractive Index Measurement and its Applications; Shyam Singh 2002 Phys. Scr. 65 167-180 doi: 10.1238/Physica.Regular.065a00167
(5) http://www.doas-bremen.de/paper/spec_euro_06_richter.pdf
(6) http://www.optek.com/Application_Note/General/English/7/Inline_Process_Color Measurement.asp
(7) http://www.coleparmer.com/techinfo/techinfo.asp?htmlfile=why-meas-viscosity.htm&ID=933
(8) Simultaneous Measurements at U-tube Density Sensors in Fundamental and Harmonic Oscillation; Krasser, E.; Senn, H.; EUROCON, 2007. The International Conference on "Computer as a Tool"; Volume, Issue, 9-12 Sep. 2007 Page(s):551-555
(9) www.tmworld.com/contents/pdf/tmw03_05D1Jr.doc
(10) http://www.omega.fr/techref/ph-6.html
(11) A new method for the determination of membrane permeability by spatially resolved concentration measurements; Bernd Schirmer et al 2004 Meas. Sci. Technol. 15 195-202 doi: 10.1088/0957-0233/15/1/027
(12) http://www.sensorland.com/HowPage037.html
(13) Sensor for measuring surface fluid conductivity in vivo; Fouke, J. M.; Wolin, A. D.; Saunders, K. G.; Neuman, M. R.; McFadden, E. R., Jr. Biomedical Engineering, IEEE Transactions Volume 35, Issue 10, October 1988 Page(s):877-881
(14) http://www.us.endress.com/eh/sc/america/us/en/home.nsf/imgref/D7A94F680B2EA516C12573A8007833A6/$FILE/T1921 C-OUSAF13.pdf
(15) Surface Plasmon Resonance Based Sensors; Springer Series on Chemical Sensors and Biosensors, Vol. 4 Homola, Jiri (Ed.) 2006, XII, 251 p. 134 illus. Hardcover ISBN: 978-3-540-33918-2
(16) Flowing thermal lens micro-flow velocimeter; Yoshikuni Kikutania, b, Kazuma Mawataria, b, Kenji Katayamaa, b, Manabu Tokeshia, b, c, Takashi Fukuzawac, d, Mitsuo Kitaokab and Takehiko Kitamor; Sensors and Actuators B; Chemical; Volume 133, Issue 1, 28 Jul. 2008, Pages 91-96
(17) Malcolm J. Crocker, Handbook of Acoustics, Ch. 4, 1998
(18) A thermoelectric sensor for fluid flow measurement, principles, calibration and solution for self temperature compensation; H. Stachowiaka, S. Lassuea, A. Dubernarda and E. Gaviotb; Flow Measurement and Instrumentation; Volume 9, Issue 3, September 1998, Pages 135-141.

Generally, and preferably, the apparatus, systems and methods of the invention are directed to or effective for identifying one or more components of an intravenous fluid during administration of the fluid to a subject using a sensor having a sensor element (e.g., with a sensing surface adapted for interaction with and being responsive to the intravenous fluid), where such sensor element (e.g., such sensing surface) is positioned at a location within an intravenous fluid system such that it interacts with the fluid (e.g., such sensing surface contacts the fluid) in relative proximity to the infusion location—the location at which the fluid enters a subject's vasculature system.

In various embodiments of various aspects of the invention, therefore, the apparatus, systems and methods of the invention comprise a sensor element (e.g., having a sensor surface) positioned proximal to (e.g., at or near) the distal end of a fluid line assembly, and/or proximal to an infusion device. For example, with reference to FIGS. 1A through 1C and to FIG. 2, such a sensor 500 can comprise a sensor element 502 which can include a sensing surface 504 in a cavity 540 of an in-line housing 530, where the in-line housing optionally has inlet 510 and outlet 520, each configured with fittings 212 (e.g., Luer Locks), and can be integrated into the fluid line assembly upstream of an infusion device 300. Alternatively, for example, and with reference to FIGS. 3A through 3C, such a sensor element 502 can include a sensing surface 504 in a cavity of a housing (hub 330) defined in infusion device 300 (e.g., catheter, needle, etc.). Preferably, with further reference to FIGS. 3A through 3C, the sensor element can be integrated into an intravenous infusion device such as a catheter. In exemplary embodiments, for example, the infusion device can have a first end adapted for fluid communication with a fluid line assembly, a second distal end adapted for insertion through the skin into the vasculature system of the subject, preferably through a peripheral vein, and a housing (e.g., the hub of a catheter) providing excorporal structural support and having a cavity providing fluid communication between the first end and the second distal end of the intravenous infusion device. For example, such housing can be integral with the hub of a catheter. One or more sensor elements can each have a sensing surface positioned within the cavity for contact with the fluid.

Optionally, in some embodiments, the apparatus, systems and methods of the invention can comprise one or more first sensor elements positioned proximal to the distal end of a fluid line assembly, and/or proximal to an infusion device, at least one fluid injection port (including for example fluid line from an intravenous pump subsystem) upstream of such first sensor elements, and one or more additional second sensor elements positioned upstream of such injection port—facilitating for example a differential measurement approach. Significantly, such second sensor element(s) can be configured to detect a baseline intravenous fluid (e.g., saline or Ringer's lactate), thereby providing a basis to compensate measurements made with the first sensor element(s) for the baseline signal, as well as for any background signal noises associated with the baseline fluid. Such a configuration can improve overall sensor sensitivity, and can thereby enable measurement and identification of components in more complex intravenous compositions. The second upstream sensors can be positioned in the intravenous fluid source container or proximal thereto, for example in a fluid line proximal to an intravenous fluid source container.

Generally, the sensors of the invention can be used in combination with one or more additional sensors, including without limitation sensors such as thermal (e.g., temperature) sensors and/or flow sensors. For examples, a thermal (e.g., temperature) sensor can include a resistance temperature detector (RTD) configured as known in the art. For example, flow sensors can include a set of two or more physically separated sensor elements, which can determine flow based on detection of a specific component at each sensor element over a measured period of time. Other known approaches for flow sensor(s) can also be effected. For example, flow sensors based on Doppler flow measurement, thermo-annemometer measurement, electro anemometer measurement and/or acoustic anemometer measurement can be effected in combination with sensors of the invention.

Generally, the one or more sensor elements can be activated using an activation circuit. The activation signal is not narrowly critical, and can comprise for example a sinusoidal or non-sinusoidal (e.g., square wave) activation signal (e.g., a voltage or current). In each case, the activation signal provided to the sensor element(s) can have a varying amplitude, a varying frequency and/or can be a pulsed signal. Non-steady or modulated wave forms, such as amplitude modulated (AM) or frequency modulated (FM) or pulse modulated (PM), or a combination of any of the foregoing can be employed. In some embodiments, the activation signal can include an alternating current (AC) signal, and can optionally further include a direct current (DC) bias signal. Such a DC bias signal can be varied during measurement of a fluid property or condition. In some embodiments, multiple frequencies can be applied and detected, serially or in some cases, simultaneously applied and detected. In some embodiments, one or more sensor elements can be activated with a broad-band "white noise" excitation signal having a wide range of continuous frequencies. Such an approach allows for detection of differences from such continuous frequencies. Other activation/excitation approaches are known in the art.

Generally, one or more sensor elements activated with an activation signal in the presence of a intravenous fluid can generate a response signal which is dependent upon or influenced by the composition of such intravenous fluid. The response signal can be conditioned (e.g., amplified, biased, etc.) for example in a (local or remote) signal conditioning processor (e.g., comprising one or more signal processing circuits), and can be optionally transmitted to a (remote or local) signal identification processor. Calibration signals can be developed and provided corresponding to known pharmaceuticals or other fluid components, or to a baseline intravenous fluid (e.g., saline or Ringers' lactate) to aid in identification of a component of an intravenous fluid. One or more identifier circuits can be effected to correlate a measured signal to a specific patient or a specific device. One or more monitoring circuits can be effected to provide for communication to a human through a user interface, and/or for comparative monitoring (e.g., against a selected setpoint). Other circuits and processors can be used, as described in further detail throughout this specification and/or as otherwise known in the art.

Multi-Parametric Approaches

Generally, and preferably, the apparatus, systems and methods of the invention are directed to or effective for identifying one or more components of an intravenous fluid during administration of the fluid to a subject using a multi-parametric approach. In such approach, multiple parameters (e.g., multiple fluid properties such as without limitation refractive index, electrochemical potential, impedance, admittance, conductivity, etc.) can be sensed, and the combination of parameters can be correlated to obtain resolution of components within the fluid. Hence, an intravenous fluid can be sensed—for example with multiple sensors (or with a sensor having multiple sensor elements) and/or with multiplexing of a sensor element to obtain independent sensing measurements—to generate a multi-parametric profile characteristic of component identity within the fluid. A multiparametric profile can be correlated to determine an identity of one or more components of the fluid. Such multi-parametric approaches advantageously provide for improved resolution of components; therefore such approaches allow for improved ability to distinguish between different fluid compositions, including for example the presence or absence of particular active pharmaceuticals, and/or various concentrations of a particular active pharmaceutical or other component.

With further reference to FIG. 4, for example, a sensor can comprise two or more sensor elements 502, each having a surface positioned within a cavity (e.g., 540, 340) of a housing (e.g., 530, 330) for contact with the fluid. The housing can be adapted for fluidic interface with a fluid line assembly of a system for intravenous delivery of fluid into a patient, or can be defined in an intravenous infusion device. As shown in FIG. 4, each of the sensor elements can be passively monitored, and/or can be activated using an activating circuit, and the response of each of the sensor elements can be acquired and processed in a processor circuit. The various responses can be correlated to identify a characteristic profile of the one or more components in the fluid. See for example, Examples 2, 3 and 4.

Generally therefore, and with further reference to FIG. 4, in preferred embodiments the apparatus, systems and methods of the invention comprise or use at least two or more sensors or an integrated assembly comprising two or more sensors (e.g., an integrated assembly comprising two or more sensor elements, each sensor element comprising one or more sensing surfaces). Preferably, such two or more sensors are of different types and/or having different sensor approaches (e.g., impedance sensor, thermal sensor, electrical property sensor, optical sensor, etc.) thereby enabling for orthogonal fluid property measurements. As a non-limiting example, such two or more sensors can include two or more of an impedance sensor (e.g., an AC impedance spectroscopy sensor), a thermal sensor, and/or an optical sensor (e.g., a refractometry sensor, a transmission sensor, an absorbance sensor, a spectrometer (including a colorimeter) or, a turbidity sensor). Preferably, such two or more sensors can be integrated into a common assembly, such as a common substrate, e.g., as part of a common sensor subunit, as discussed below in connection with FIG. 6C through FIG. 6G. As a non-limiting example, two or more of an impedance (e.g., AC impedance) sensor, a thermal (e.g., a resistance thermal detector) sensor, and an optical (e.g., refractive index) sensor can be employed in combination.

In a preferred embodiment, at least one sensor is an electrical properties sensor such as an impedance sensor. Independent electrical property (e.g., impedance) measurements can be derived, for example, from a set of two or more sensor elements having sensing surfaces defined by electrodes consisting essentially of different metal materials. Preferred metals include noble metals and other chemically inert transition metals, such as without limitation, Au, Pt, Pd, Ag, W, Ti, Ni, Sn, Co and others. Electrical property measurements such as impedance measurements can preferably be effected using different pair combinations of three or more sensor elements. For example, for a sensor comprising sensor elements A, B and C, three pairs of sensor elements can be used: an A-B pair, an A-C pair, and a B-C pair, with each of such pairs defining an independent impedance measurement channel. As another example, for a sensor comprising five sensor elements A, B, C, D and E, such five sensor elements can be paired to define ten independent impedance measurement channels: A-B, A-C, A-D, A-E, B-C, B-D, B-E, C-D, C-E, and D-E. Such impedance sensor elements can be activated using alternating current (AC), allowing for determination of both real and imaginary (complex) impedance response for each pair of sensor elements. Hence, three sensor elements can provide for six independent measurement channels at each applied AC frequency for determining the identity of a component of the intravenous fluid. Generally, the number of discrete independent impedance sensor elements can range from 2 to 100, from 2 to 50, from 2 to 20 or from 2 to 10. Pairs of sensor elements can be activated using multiple (different) frequencies. If five frequencies are used for activating an impedance sensor comprising three sensor elements, for example, then the impedance sensor effectively provides for thirty independent measurement channels for determining the identity of a component of the intravenous fluid (three sensor elements→three channels×real and imaginary components→two channels=six channels per frequency×five frequencies→thirty channels). Generally, the number of discrete independent frequencies can range from 1 to 100, preferably from 2 to 100, from 2 to 50, from 2 to 20, from 2 to 10 or from 2 to five or from 2 to 3. Similarly, pairs of sensor elements can be activated at multiple (different) amplitudes, with a similar multiplier effect on multi-modal measurements. Generally, the number of discrete independent amplitudes can range from 1 to 100, preferably from 2 to 100, from 2 to 50, from 2 to 20, from 2 to 10 or from 2 to five or from 2 to 3. Further variations, such as use of different input signals—sinusoidal, step-wave, pulse, etc. —can provided for additional independent channels in a multiparametric context.

Analogous multiplexing can be effected with other sensors types (e.g., optical, electrochemical potential, etc.).

Processing of the signal acquired from each of a plurality of sensors can be effected in a signal identification processor. Such processor can comprise signal conditioning circuits for conditioning one or more signals (e.g., for amplifying, biasing) prior to or during further processing. Such processor can employ software or firmware or can include an application specific integrated circuit (ASIC) effective for and/or adapted to recognize and distinguish between signals correlating to components of an intravenous fluid. Such software can comprise pattern recognition algorithms known in the art. In one relatively simple algorithm, for example, sensor signals can be processed to recognize the identity of component substances by measuring produced deviations—e.g., in various directions by supplying the values for the expected angles. See for example, Example 4. See also for example, J. Ross Macdonald, Impedance Spectroscopy Theory, Experiment, and Applications (2005).

For example, in embodiments where a set of two or more sensor elements having sensing surfaces defined by metal electrodes are exposed to a fluid, and activated by energizing with an AC voltage or current, the resulting complex current or voltage can be measured. When the activating signal is sufficiently small, the system can respond linearly, and may be modeled in terms of complex AC impedance or admittance, e.g. having real (x) and imaginary (y) response components. The measured values of x and y as well as their relative magnitude change predominantly with the electrical properties of the fluid flow and fluid-electrode interface, both of which are heavily affected by the composition of the flow. The change in these values can be correlated to the nature of the fluid material and can be used to identify the particular component of the intravenous fluid. As demonstrated in Example 4, for example, highly diluted components injected into saline flow can be identified by such sensors. Generally, a deviation distance from a data point corresponding to pure saline or Ringer's lactate depends on both concentration and molecular or ionic composition of the component, while deviation direction from such data point depends predominantly on the molecular or ionic composition of the component. For higher concentrations of the component, both magnitude and direction of the deviation become concentration-dependent in unique and distinguishable manner which is specific to and dependent upon the particular component added to the saline. Hence, such deviation dependencies enable identification of components having different compositions or concentrations. For example, pattern recognition algorithms can be adapted to recognize substances that are components of an intravenous fluid. A data signal from sensors can result in deviations from baseline data corresponding to the background composition of the intravenous fluid (e.g., saline or Ringer's lactate), including deviations in magnitudes and/or deviations in directions, the angles for each of which can be determined as described above and exemplified in Example 4. In subsequent operation, such software can compare measured angles determined from detected data with the values for expected angles corresponding to certain substances, thereby identifying the substances. Such pattern recognition algorithms can be advantageously applied to the differentiation and recognition of data generated by the sensors in multi-dimensional space. Additionally, software can be used to determine the cumulative dosing of a component of a fluid, as well as a projected dosing over a certain upcoming period of time. For example and without limitation, once a component is identified, a current cumulative dosing level can be measured by integrating the signal corresponding to that component over time during the period defined from when the signal exceeded a detection threshold to the current time (e.g., taking into account the sensor sensitivity to identified substance and the volumetric flow). Projected dosing levels can extrapolate the component composition and extend the time period for a defined period.

Adaptations on such algorithms are known in the art. Moreover, more elaborate pattern recognition algorithms can be applied to the differentiation and recognition of curves generated by the multiparametric sensor system in multi-dimensional space. See, for example, Sing-Tze Bow, Pattern Recognition and Image Preprocessing (2002); M. S. Nixon, A. S. Aguado, Feature Extraction and Image Processing (2002); and D. Maltoni, D. Maio, A. K. Jain, S. Prabhakar, Handbook of Fingerprint Recognition, 2002. Examples of other pattern recognition software include without limitation artificial neural network and fuzzy logic algorithms.

Preferred Circuit Configurations/Monitoring Approaches

Generally, and preferably, the apparatus, systems and methods of the invention are directed to or effective for identifying one or more components of an intravenous fluid during administration of the fluid to a subject (e.g., a specific patient, for example at a hospital, clinic, surgical environment, home hospice, nursing home, assisted living environment, etc), where such subject is positively and specifically identified in connection with monitoring and administration of the intravenous fluid. Various embodiments and aspects of the invention can include approaches for correlating the sensor data (i.e., data (e.g., as represented by a signal) originating from the sensor—either raw data or more typically processed data) to a specific subject (e.g., patient). For example, the sensor (or apparatus or system comprising a sensor) can include an identifier circuit for correlating sensor data to a specific subject. Typically, and preferably, such identifier circuit may be in communication with one or more other circuits, including for example circuits for receiving processing, storing, displaying or transmitting data, including data originating from the sensor element, such as a signal processing circuit or a data retrieval circuit. Such integrated patient-identification approaches can further enhance the benefit to patient safety, by reducing the potential for errors associated with intravenous administration, and especially intravenous drug administration.

Generally, and preferably, the apparatus, systems and methods of the invention are directed to or effective for identifying one or more components of an intravenous fluid during administration of the fluid to a subject with a remote and/or centralized monitoring approach. Although such remote and/or centralized monitoring approaches can be effected for an individual subject (e.g., in a home hospice environment), such approaches are especially advantageous in connection with multi-subject care environments. For example, different sensor data from one subject or from several different subjects (in each case, such sensor data being locally generated and specifically associated with an intravenous fluid being administered to a particular subject) can be acquired and/or monitored at a location which is remote (relative to the patient)—such as a nursing station; preferably such sensor data can be centrally monitored at such remote location. In various aspects and embodiments therefore, and with reference to FIGS. 1B and 1C, FIG. 2, and FIGS. 3A through 3C, for example sensor data, can be generated in a processor 550 local to and in communication with a sensor element 502 (e.g., having a sensing surface in contact with the intravenous fluid), preferably for each of two or more subjects, and then such locally-generated sensor data stream(s) can be acquired by a processor 600 remote from the sensor element 502. Such acquisition can be effected, for example, via wireless (e.g., Bluetooth®) or other communication approaches. The local processor 550 can be in communication with the sensor element 502, and particularly with a sensing surface 504 thereof, for example through one or more releasable contacts 508 and one or more electrical connections 506. The local processor 550 can be permanently integrated or intermittently integrated (temporally limited engagement) with the sensing element 502 as described below.

The remote processor 600 can comprise one or more circuits for receiving, processing, storing, displaying or transmitting the acquired sensor data. The acquired sensor data can be monitored remotely, including for example at a central monitoring location. Preferably for example, the monitoring can be done visually by human interaction with a display and/or can be further enhanced and effected by various automated approaches. In one such automated monitoring approach, a monitoring circuit can comprise a data comparator module for comparing one or more parameters (e.g., data values) derived from sensor data with one or more parameters (e.g., data values) which are prescribed or proscribed for a particular subject (e.g. patient). Such patient-relevant parameters can be treatment-centric (e.g., applicable to all such patients undergoing a particular treatment), including semi-customized treatment-centric parameters which include a patient-specific data input (e.g., a patient weight, patient age, etc.) to determine a treatment-centric parameter, and/or such patient-relevant parameters can be patient-centric (e.g., wholly customized for a specific patient). Exemplary non-limiting parameters can include dosing levels, dosing timing (onset or completion), dosing frequency, etc. for various and specific active pharmaceutical agents or other components of an intravenous fluid. Patient-relevant parameters can be specific for the intravenous monitoring system effected by the apparatus, systems and methods of the invention, and/or can be common with (e.g., shared with) various other systems, such as infusion pump systems (e.g., "smart pumps"). Advantageously, the monitoring approaches of the apparatus, systems and methods of the invention can also include certain notice (e.g., alarm) features—to provide notice to a caregiver that a specific patient's intravenous fluid delivery system is operating incongruous with a prescribed or proscribed treatment, and/or can also include certain corrective action (e.g., system control) features—to make, preferably automated, a corrective action with the intravenous fluid delivery system. For example, upon determining an inconsistency between corresponding sensor-data-derived parameter and prescribed or proscribed patient-relevant parameter, an alarm can sound and/or a control circuit can activate a control element (e.g., an automated infusion valve) to make a change in the intravenous administration regime. Such remote and/or central monitoring approaches can further enhance the benefit to patient safety, by reducing the potential for errors associated with intravenous administration, and especially intravenous drug administration.

Generally, and preferably, the apparatus, systems and methods of the invention are directed to or effective for identifying one or more components of an intravenous fluid during administration of the fluid to a subject with a sensor that comprises a processor (e.g., as included within a processor assembly) which is physically separable from, and intermittently interfaceable with (e.g., for a finite, operationally effective period of time) a sensor element (e.g., as included within a housing assembly). The approach of a temporally-limited engagement (interfacement) of the processor and the sensor element allows for regular operation while engaged/interfaced, and allows for physical separation of sensing function and processing function of a sensor (at least for some period of time) after or between operations, with a corresponding separation of physical treatment of the embodiments which effect such function. For example, and with reference to FIG. 1B, FIG. 2, and FIGS. 3A through 3C, the sensor element 502 can be physically separated from the processor 550 for a period of time to allow for sterilizing the sensor element 502 (or a sensing surface 504 thereof) or for disposal and replacement of a (pre-) sterilized sensor element 502 (or a sensing surface 504 thereof). Such separation also allows for re-use of the processor 550—for example, in connection with a second subsequent subject. The processor 550 can be engaged for example through a processor guide 552. Significantly, since processors 550 are generally more expensive than sensor elements 502 (or sensing surfaces 504 thereof), the re-use of processors 550 in such a temporally-limited engagement (interfacing) approach provides for efficiency of capital investment, especially in a multi-subject (e.g., hospital, surgical, nursing care, etc.) environment.

In any of the aforementioned approaches and in any of the aspects and embodiments of the invention, the monitoring system can include a logging circuit for recording (e.g., storing) sensor data over time. The logging circuit can be in accessible communication with a display circuit for intermittent (temporally-limited) display of sensor data or of a patient-relevant parameter derived from sensor data. In operation, for example, the logging circuit can record sensor data without displaying such data (or a patient-relevant parameter derived therefrom) unless and until specifically requested (e.g., by a caregiver based on that caregiver's discretion, and/or by another circuit, such as by the comparator module of the monitoring circuit when there is an incongruity between a sensor data parameter and a prescribed or proscribed patient-relevant parameter) to be displayed. Display, such as automated display during an abnormal operational event can help a caregiver understand a situation more quickly and thereby reduce the risk of a compounded error and improve the corrective treatment regime. Additionally or alternatively, such display can be effected ex-post facto to reconstruct facts regarding the patient experience based on logged sensor data.

Figure 5A:
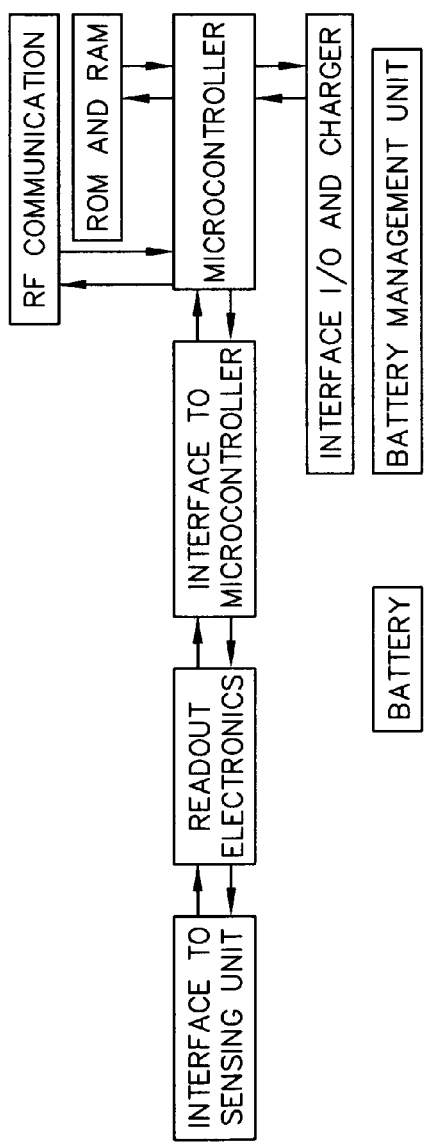
FIG. 5(A-E) illustrate schematic representations of various circuits associated with sensors of various aspects and embodiments of the inventions, including independently: a block diagram of a specific preferred circuit configuration (FIG. 5A); a high-level schematic diagram showing a sensor element configured in an assembly such as a housing assembly, and various circuits being configured in an assembly such as housing assembly, and/or in a local processor and/or in a remote processor (FIG. 5B); and additional high-level schematic diagrams showing alternative configurations for a system comprising (i) a (one or more) sensor element, (ii) a signal-conditioning processor, including one or more circuits adapted for conditioning (e.g., amplifying) a signal, and (iii) a signal-identification processor, including one or more circuits adapted for identifying or determining a signal representative of the identity of one or more components of an intravenous fluid (e.g. as corresponding to a component within a composition or concentration of a component within a composition) (FIG. 5C through 5E).
Figure 5B:
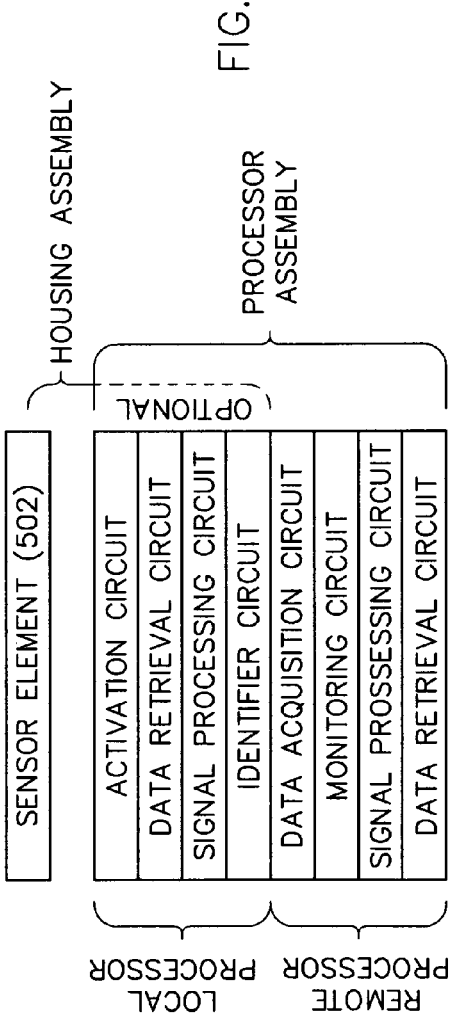

Various preferred schema for circuit configuration and operation are shown in FIGS. 5A and 5B. With reference to FIG. 5B illustrated is a high-level schematic diagram showing various circuits and one arrangement for their interrelationship with local processor and remote processor, and/or with housing assembly and processor assembly. FIG. 5A illustrates a block diagram of a specific preferred circuit configuration for a reader unit comprising a microcontroller. The circuits of such reader unit can include, for example, one or more of any of an activation circuit, a data retrieval circuit, a signal processing circuit, an identifier circuit, a data acquisition circuit, and/or a monitoring circuit. Preferably, one or more of any such circuits can be adapted into a signal conditioning processor and/or a signal identification processor. Such circuits can be included, for example, in a processor assembly for intermittently interfacing/temporally-limited engagement with a sensor element. Alternatively, some of such circuits could be in a housing assembly—see for example FIG. 5B. Preferably, with reference again to FIG. 5A, the reader unit can be programmed when a patient is admitted for treatment. The reader unit can receive and store the identification information about the patient either through RF interface or through I/O interface from the admitting database information, for example in an identifier circuit. The reader unit can be physically co-located adjacent to or attached to the patients, for example as a bracelet, or adhesively attached to a patient's skin. Once the identification information is received, and the processor assembly is interfaced with a housing assembly (described herein), the reader unit can commence broadcasting identifier information, for example wirelessly via RF interface such as WiFi or Bluetooth® interface, continuously or periodically. Alternatively the unit can be connected via direct connection (e.g., electrical wire or optical cable) to a bedside monitoring system, which can itself send patient identification information through I/O interface. Along with patient identification information the unit can also send information regarding the status of the interface between the processor assembly and the housing assembly (e.g., whether engaged (operable) or disengaged (non-operable). Once a patient has received an intravenous line, and when the unit is engaged for operation, through the interface to the sensing unit—the reader can verify the connection, energize or activate the sensors, and sense and transmit data from the sensor element, and preferably from a local processor to a remote processor included within a monitoring unit, for example via any suitable communication approach such as hospital radio frequency port; alternatively the monitoring can be local, such as via bedside monitoring equipment.

Figures 5C, 5D, 5E:
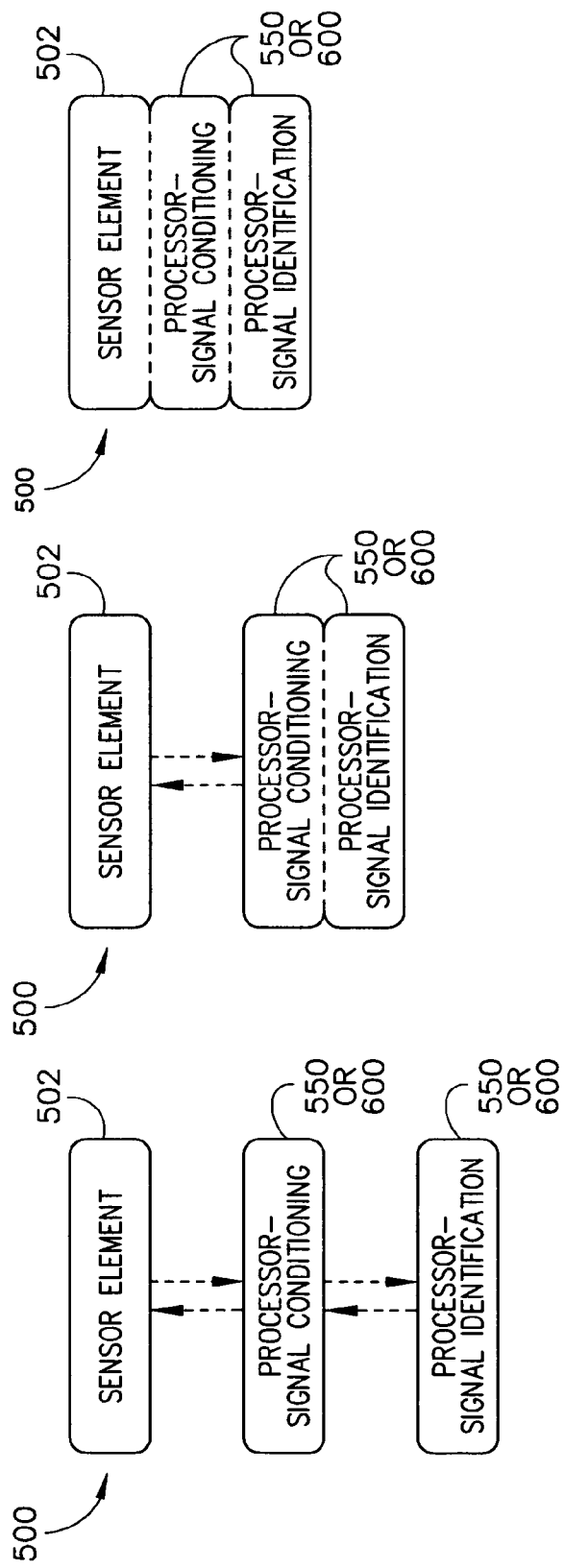

Additional preferred schema for an integrated sensor and circuit configuration are shown in FIGS. 5C through 5E. Generally, such configuration can include a sensor that comprises (i) an assembly comprising one or more sensor elements 502, (ii) a signal-conditioning processor (e.g., optionally included within a local processor 550 (which can, optionally, be physically separable from and/or be intermittently interfaceable with the sensor element 502) or included within a remote processor 600), and (iii) a signal-identification processor, including one or more circuits adapted for identifying or determining a signal representative of the identity of one or more components of an intravenous fluid (e.g., optionally included within a local processor 550 (which can, optionally, be physically separable from and/or be intermittently interfaceable with the sensor element 502) or included within a remote processor 600). With reference to FIG. 5C for example, in one such preferred subembodiment, each of the assembly comprising the one or more sensor elements 502, the signal-conditioning processor (550 or 600), and the signal-identification processor (550 or 600) are each physically separate components. In an alternative of such preferred subembodiment, represented schematically in FIG. 5D, the assembly comprising the one or more sensor elements 502 is physically separate from an integrated assembly comprising the signal-conditioning processor (550 or 600) and the signal-identification processor (550 or 600). In another subembodiment shown in FIG. 5E, each of the one or more sensor elements 502, the signal-conditioning processor (550 or 600), and the signal-identification processor (550 or 600) are integrated into a common (integrated) assembly. Such various approaches for configuring the sensor elements, the signal-conditioning processor and the signal-identification processor are preferred, an can be generally used with any aspects, embodiments and approaches described herein.

Figure 6A:
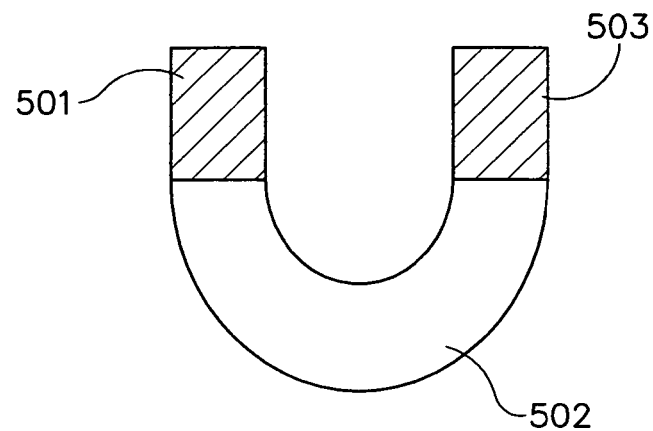
FIG. 6 (A-G) illustrate schematic representations of various sensors, including an optic fiber refractive index sensor (FIG. 6A), an electrochemical potential sensor (FIG. 6B), and various schematic views of an integrated assembly comprising impedance and refractive index sensor elements (FIG. 6C through FIG. 6G), including a perspective view of the integrated sensor element assembly (FIG. 6C), a top-plan view of a first surface of a first substrate thereof (FIG. 6D), a detail of the sensing surfaces of the impedance sensor elements as shown therein (FIG. 6E), a perspective assembly view of the first substrate and a second substrate, shown with a functional communication port, such as a USB port (FIG. 6F), and a perspective view of the (assembled) integrated assembly of impedance/refractive index sensor elements (FIG. 6G).
Figure 6B:
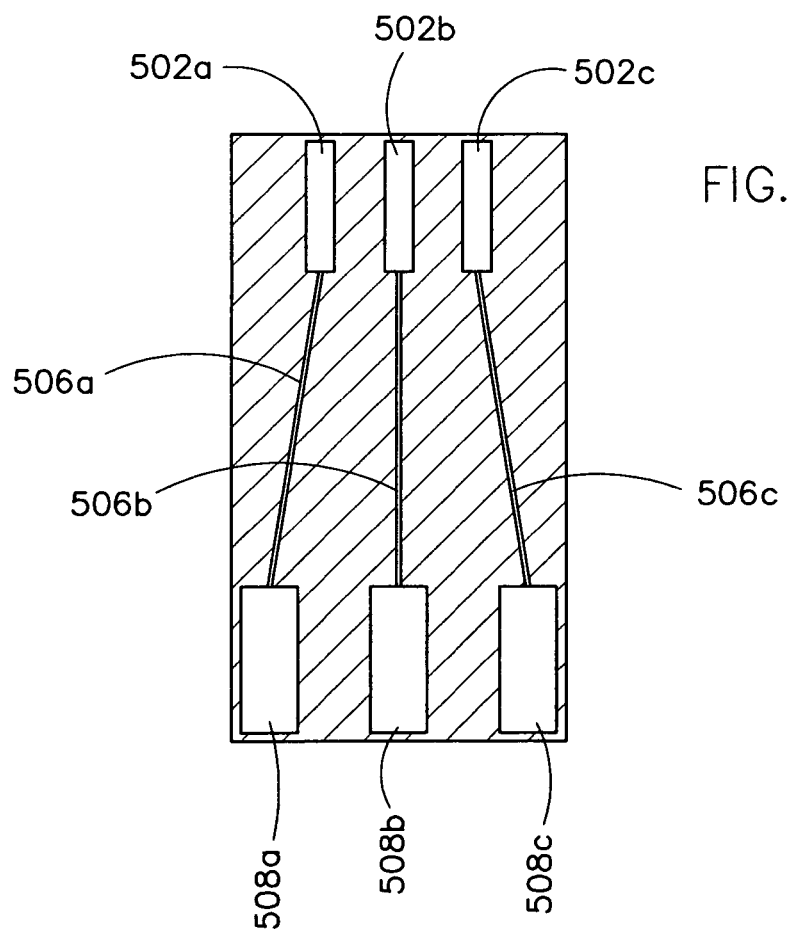
Figure 6D:
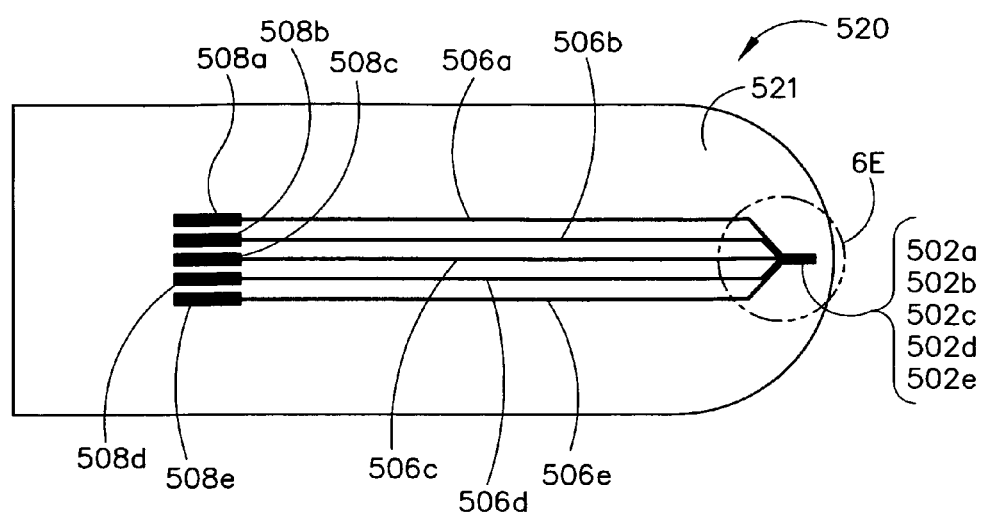
Figure 6E:
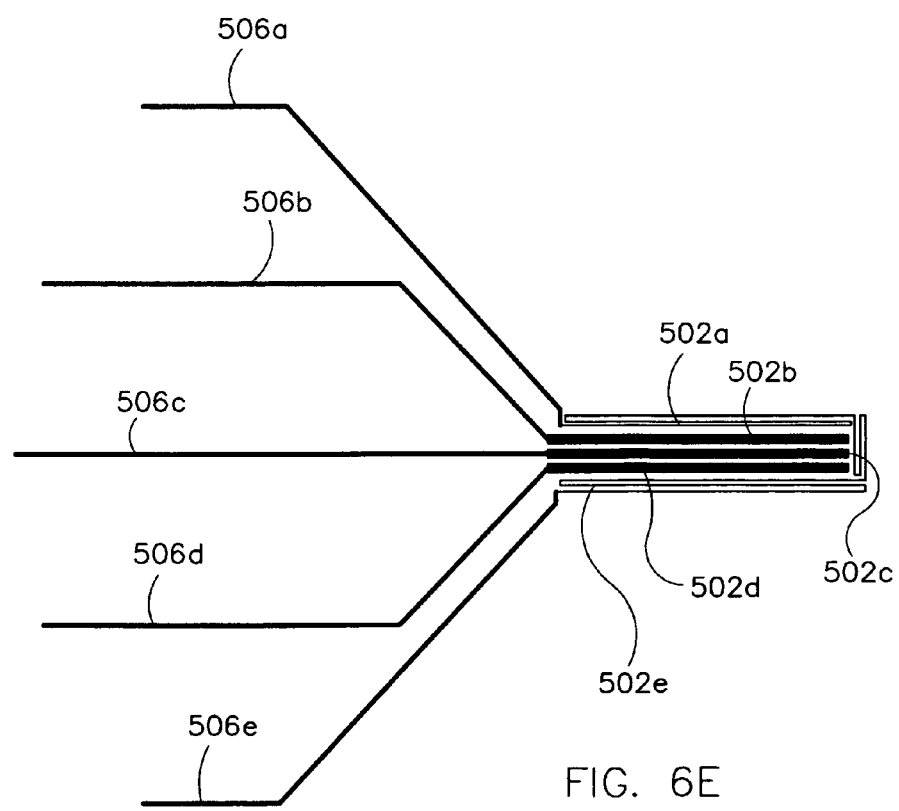

FIG. 6 (A, B) illustrate schematic representations of various sensors, including an optic fiber refractive index sensor (FIG. 6A) and an electrical property sensor (e.g., which can be configured and employed, for example, as an impedance sensor or for example, as an electrochemical potential sensor) (FIG. 6B). Such sensors and others described herein are known in the art. Briefly, with reference to FIG. 6A, an optical sensor can comprise a fiber optic, such as a flexible fiber optic formed in a U-shape, and having an optical entrance 501, a sensor element 502 defined by the curved region of fiber optic exposed to the intravenous fluid, and an optical exit 503 into a detector. In operation, a light can be admitted to the fiber optic, guided to the sensor element 502 and exposed to an intravenous fluid in communication with the sensor element 502. Variations in intensity of the light coupled from the entrance to exit are proportional to the refractive index of the fluid. The index of refraction can be fluid-composition variable, thereby providing a parameter for determining the identity of the fluid composition. See, for example, Examples 1, 2 and 3. Referring further to FIG. 6B, an electrical property sensor (e.g., impedance sensor, electrochemical potential sensor, etc.) can comprise a plurality of sensor elements 502*a*, 502*b*, 502*c*. For example, each of the sensor elements can comprise a sensing surface consisting of a material such as a metal, with the sensing surface of each such sensor element being the same material, or in some embodiments a different material, such as a different metal. Preferably, metal materials are chemically inert within the fluid environment. Preferred metals include noble metals and other chemically inert transition metals, such as without limitation, Au, Pt, Pd, Ag, W, Ti, Ni, Sn, Co and others. Each of the sensor elements 502*a*, 502*b*, 502*c* are in electrical communication with dedicated corresponding contacts 508*a*, 508*b*, 508*c*, respectively, for example, through dedicated corresponding electrical connectors 506*a*, 506*b*, 506*c*. The sensor elements 502, contacts 508 and electrical connectors 506 can be formed or supported on a common substrate, such as common microfabrication substrate. In operation, the electrical property (e.g., impedance or electrochemical potential) associated with each of the sensor elements 502*a*, 502*b*, 502*c* can be measured independently and simultaneously, proving for three independent real-time channels for multiparametric characterization of a component within an intravenous fluid.

Figure 6G:
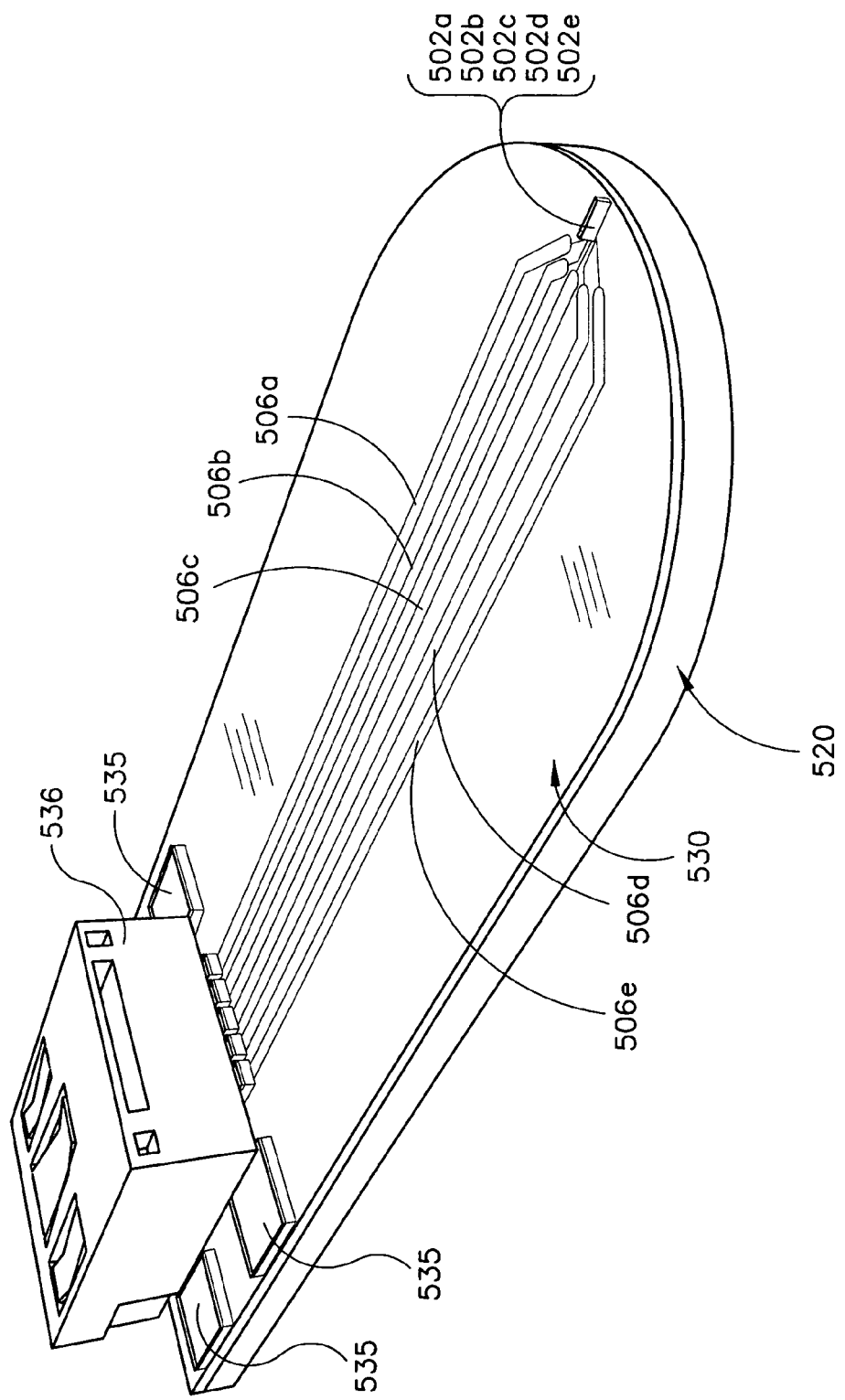

A preferred sensor embodiment can comprise an integrated assembly comprising two or more sensor elements, such as impedance sensor elements, thermal sensor elements and/or refractive index sensor elements. With reference to FIG. 6C through FIG. 6G, for example, an integrated sensor assembly can comprise one or more substrates, such as a first sensor element substrate 520 and comprising two or more sensor elements. The first sensor element substrate 520 can have a first (top as shown) surface 521 and a second (bottom as shown) surface 522. As depicted, and with specific reference to FIG. 6C, FIG. 6D and FIG. 6E (showing detail of tip portion of the sensor element substrate of FIG. 6D) for example, the first substrate can comprise impedance sensor elements 502*b*, 502*c*, 502*d*, and also thermal sensor elements 502*a*, 502*e*. The impedance sensor elements 502*b*, 502*c*, 502*d*, and the thermal sensor elements 502*a*, 502*e*, can each comprise a sensing surface defined by a metal electrode. The metal electrode preferably consists essentially of a chemically inert, conductive material. Metals or metal compositions comprising noble metals and other transition metals are preferred. Examples include Au, Pt, Pd, Ag, W, Ti, Ni, Sn, Co and others. Preferably, the impedance sensor elements 502*b*, 502*c*, 502*d* each comprise a sensing surface defined by different types of metals (e.g., where 502*b*, 502*c*, 502*d* have a sensing surface defined by electrodes consisting essentially of Au, Pt, Pd, respectively). The thermal sensor elements 502*a*, 502*e* can each comprise a sensing surface defined by the same type of metal (e.g., Au). Electrical connectors 506*b*, 506*c*, 506*d* provide a conductive path (for signal communication) between impedance sensor elements 502*b*, 502*c*, 502*d* and corresponding contacts 508*b*, 508*c*, 508*d*, respectively. Similarly, electrical connectors 506*a*, 506*e*, provide a conductive path (for signal communication) between thermal sensor elements 502*a*, 502*e*, and corresponding contacts 508*a*, 508*e*, respectively. As depicted, and with specific reference to FIG. 6C, the first substrate 520 can also comprise a refractive index sensor element 502' integrally configured within the body of the first substrate 520. As shown for example, such refractive index sensor element can comprise an optically transparent region of the substrate 520 defining a wave guide 524, 525, 526, and further defined by a region 528 of the substrate which is optically less transparent or substantially non-transparent. With specific reference to FIGS. 6F and 6G, the integrated sensor assembly can further comprise a second capping substrate 530 having a first (top as shown) surface 531 and a second (bottom as shown) surface 532. The second capping substrate 530 can be adapted with an aperture situated over and providing for fluid access to sensor elements 502*a*, 502*b*, 502*c*, 502*d*, 502*e*, and being further adapted with apertures situated over and providing electrical access to each of the contacts 508*a*, 508*b*, 508*c*, 508*d*, 508*e*. In the configured sensor assembly, the first (top) surface 521 of the first sensor element substrate 520 can be capped/sealed by integral contact with the second (bottom) surface 532 of the second capping substrate 530. Fabrication of such integrated subassembly can be facilitated by alignment pads 535 on the first surface 521 of the first substrate 520 and spatially corresponding apertures in the second capping substrate 530. As shown in FIG. 6F and FIG. 6G, the integrated sensor assembly can further comprise a functional communication port 536, such as a USB port, providing independent electrical communication with each of the contacts 508*a*, 508*b*, 508*c*, 508*d*, 508*e*.

In operation, with reference to FIGS. 6C and 6G, an intravenous fluid being measured can be in fluid communication with the curved tip portion of the integrated sensor assembly. The impedance sensor elements 502*b*, 502*c*, 502*d* can be activated using an activation circuit in electrical communication with these sensor elements through communication port 536, contacts 508*b*, 508*c*, 508*d* and electrical connectors 506*b*, 506*c*, 506*d*, respectively. A responsive signal can be received from each of these sensor elements by a data retrieval circuit in electrical communication therewith through the same independent communication paths. Three independent channels can be configured for impedance measurements—using different pairs of impedance sensor elements in combination—namely: (i) 506b-506c; (ii) 506c-506d; and (iii) 506b-506d. Each of such pairs of sensor elements can be activated using alternating current (AC), allowing for determination of both real and imaginary (complex) impedance response for each pair of sensor elements. In this configuration therefore, the impedance sensor can effectively provide for six independent measurement channels at each applied AC frequency for determining the identity of a component of the intravenous fluid. These pairs of sensor elements can be activated using multiple frequencies. If five frequencies are used for impedance sensor element activation, for example, then the impedance sensor effectively provides for thirty independent measurement channels for determining the identity of a component of the intravenous fluid. The thermal sensor elements 502a, 502e can be variously configured, for example for measuring temperature and or flow (e.g., as a thermal flow anemometer). In one embodiment for example, thermal sensor elements 502a, 502e are configured as a resistance temperature detector (RTD), and can be activated using an activation circuit in electrical communication with these sensor elements through communication port 536, contacts 508a, 508e and electrical connectors 506a, 506e, respectively. A responsive signal can be received from each of these sensor elements by a data retrieval circuit in electrical communication therewith through the same independent communication paths. The refractive index sensor can be used simultaneously and in combination with the impedance sensor elements 502b, 502c, 502d, and the thermal sensor elements 502a, 502e. With reference to FIG. 6C, for example, incident light (e.g., from an infrared light emitting diode (LED) source) can be admitted through an inlet end into a first section 524 of the wave guide, and allowed to interact with the intravenous fluid in a second section 525 of the wave guide which defines the refractive index sensor element 502'. The efficiency of light coupled through the waveguide is affected by refractive index of a fluid into which the waveguide is immersed; the resulting signal is proportional to the fluid refractive index. Light can be retrieved through a third section 526 of the wave guide at an outlet end of the wave guide into a photo-sensitive detector (for example into an infrared phototransistor) configured for detecting the output light. A multimeter (e.g., a Keithley Model 2100 Multimeter) can measure voltage output of the photo-sensitive detector, and such output signal can be communicated to a data retrieval circuit. Generally, each of the signals received from the impedance sensor elements, thermal sensor elements, or refractive index sensor element can be independently conditioned (e.g., amplified, biased, etc.) in signal processing circuit within a (e.g., local or remote) signal conditioning processor, and can processed in a signal identification processor (e.g., local or remote), for example using multiparametric analysis, to identify a component of the intravenous fluid. The identified component can be correlated to a specific patient through use of an identifier circuit, as described above.

EXAMPLES

Example 1

General Methods for Identifying Components Typical of an Intravenous Fluid

In this example, materials were obtained from Sigma Aldrich and dissolved or diluted with 0.9% saline to reach the desired concentrations. Solutions of insulin, heparin and potassium chloride were prepared at concentrations comparable to typical bolus doses used in medical settings. All experiments were carried out using prepared solutions contained in 20 ml glass vials. Samples were measured by dipping admittance and optical sensor probes into each vial such that the active area of each probe was fully submerged in the solution to be tested. The response of each sensor to air and tap water were also measured.

The admittance signal is measured using a probe constructed with noble metal pads embedded in a polymer substrate. All measurements were performed at a frequency of 100 kHz. An Agilent Model 4395A network analyzer was utilized for measuring the admittance probe.

The optical sensor is constructed from a section of optic fiber with an infrared LED fed into one end and an infrared phototransistor detecting the output at the opposite end. The fiber jacket is removed along a section of its length and this section is bent into a curve. In this configuration, the efficiency of light coupled through the fiber is affected by refractive index of a fluid into which it is immersed and the resulting signal is inversely proportional to the fluid refractive index. A Keithley Model 2100 Multimeter was used to measure the voltage output of the optical sensor phototransistor detector and all data is recorded using a PC.

Example 2

Identification of Various Active Pharmaceutical Agents and Other Components Typical in an Intravenous Fluid The sensor configuration and method described in Example 1 was used to identify components typically included in intravenous fluids, including pharmaceutical agents and other components. Specifically, the methods were applied to identify potassium chloride (KCl), sodium chloride (saline) (NaCl), heparin, water, insulin and air using admittance and refractive index sensors.

Figure 7A:
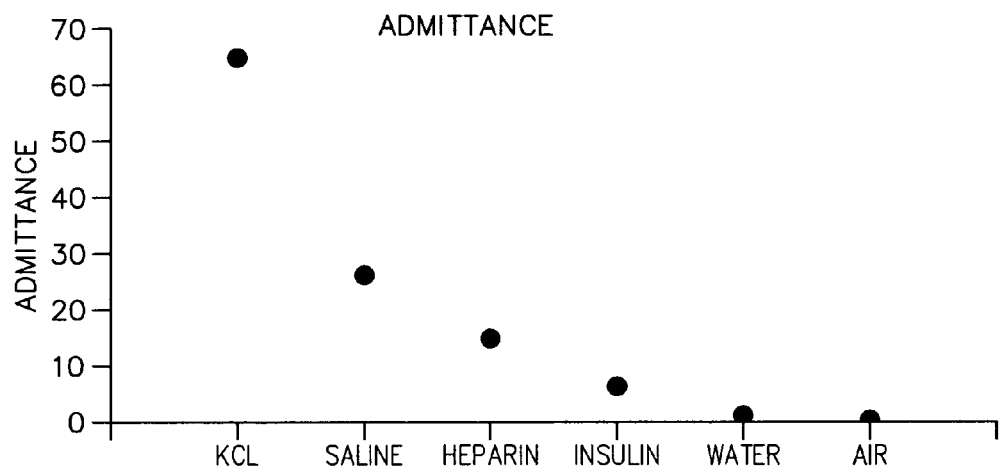
FIG. 7 (A-D) illustrate various data derived from Example 2, including plots of measurements of admittance, real portion (FIG. 7A), admittance, imaginary portion (FIG. 7B), optical refractive index (FIG. 7C), and a multi-parametric representation of such measurements (FIG. 7D).
Figure 7B:
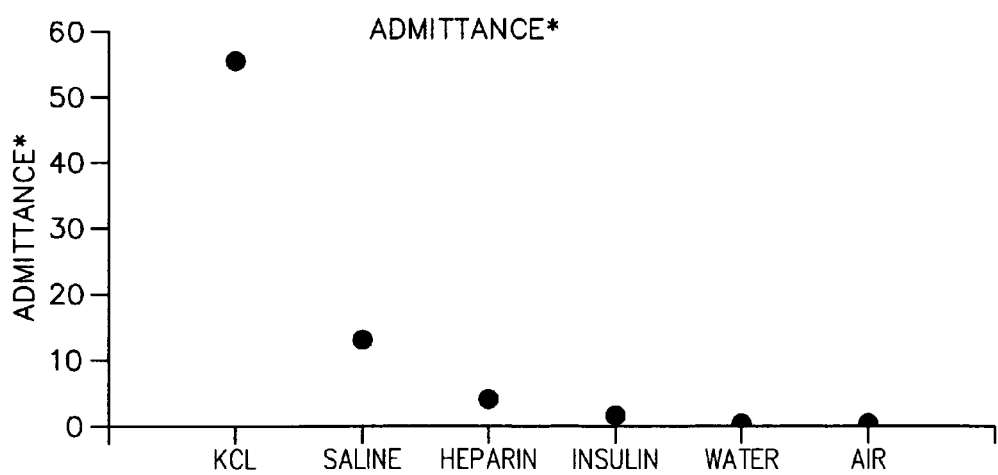
Figure 7C:
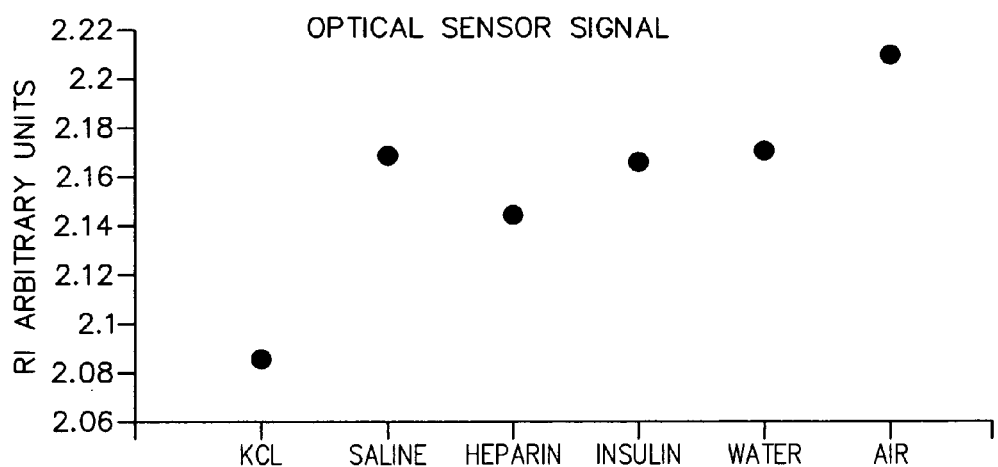

The results are summarized in Table 3, and shown graphically in FIGS. 7(A-C) for measurements of admittance, real portion (FIG. 7A), admittance, imaginary portion (FIG. 7B), optical refractive index (FIG. 7C).

Figure 7D:
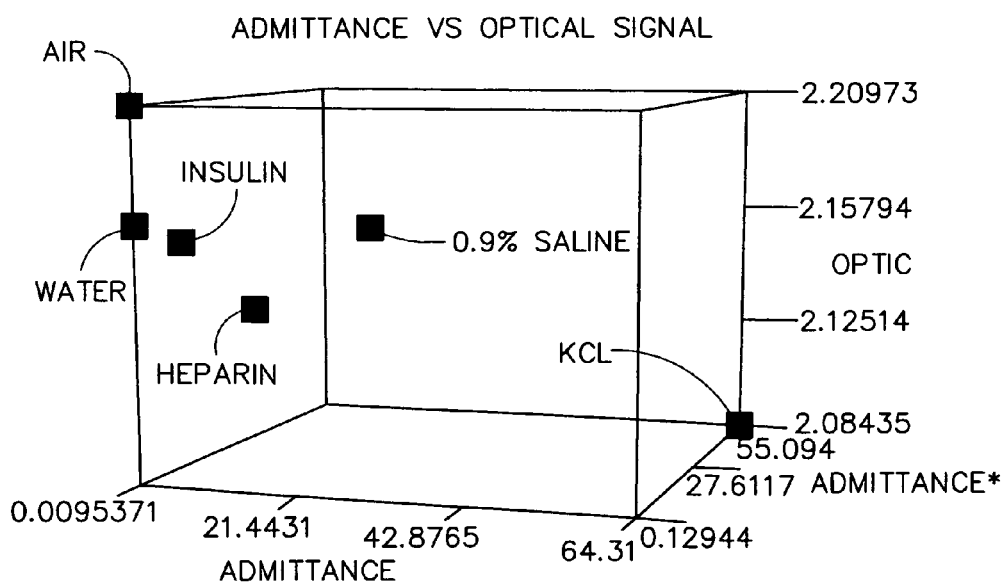

A multi-parametric representation of such measurements is shown in FIG. 7D. As observed from these results, the multi-parametric analysis and data provide improved resolution of the various components of the intravenous fluid, and therefore allow for a more robust approach for distinguishable measurement thereof. The multi-parametric profile can be characteristic of the fluid component.

TABLE 3

Sensor Responses for Various Components

| Material | Admittance | Admittance* | Optical Signal |
|---|---|---|---|
| KCL | 64.310 | 55.094 | 2.084 |
| Saline | 25.368 | 12.800 | 2.168 |
| Heparin | 14.200 | 3.775 | 2.144 |
| Water | 0.481 | 0.129 | 2.171 |
| Insulin | 5.857 | 1.339 | 2.166 |
| Air | 0.010 | 0.141 | 2.210 |

Note 1:
The optical signal is inversely proportional to refractive index.
Note 2:
Admittance denotes the real admittance.
Note 3:
Admittance* denotes the imaginary (complex) admittance.

Example 3

Identification of Component Typical of Intravenous Fluid in Dilution Series

A set of dilution series experiments were conducted, in which concentrated samples of heparin, insulin and potassium chloride were each diluted by half concentration a total of three times to give concentrations of 1, V£, %, and ⅛ of a typical bolus dose and each one measured using the admittance and optical sensors described in Example 1 according to the approach described in Example 1.

The data for each dilution series of heparin, insulin and potassium chloride are shown in Tables 4A, 4B and 4C, respectively. Concentration is relative dilution. Admitt.=Admittance (real portion). Admitt.*=Admittance (imaginary portion).

Figure 8A:
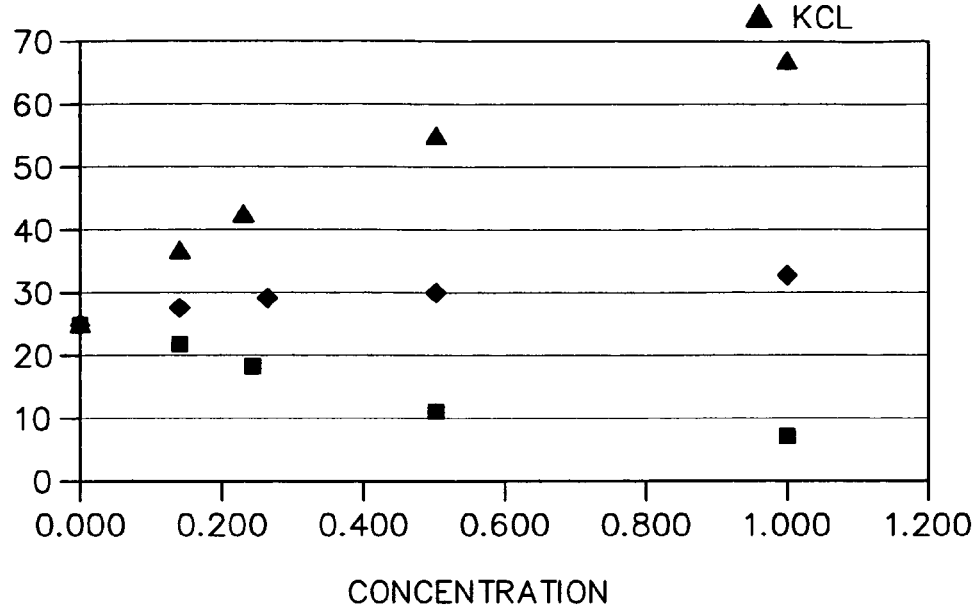
FIG. 8 (A-D) illustrate various data derived from Example 3, including plots of measurements of admittance, real portion (FIG. 8A), admittance, imaginary portion (FIG. 8B), optical refractive index (FIG. 8C), and a multi-parametric representation of such measurements (FIG. 8D).
Figure 8B:
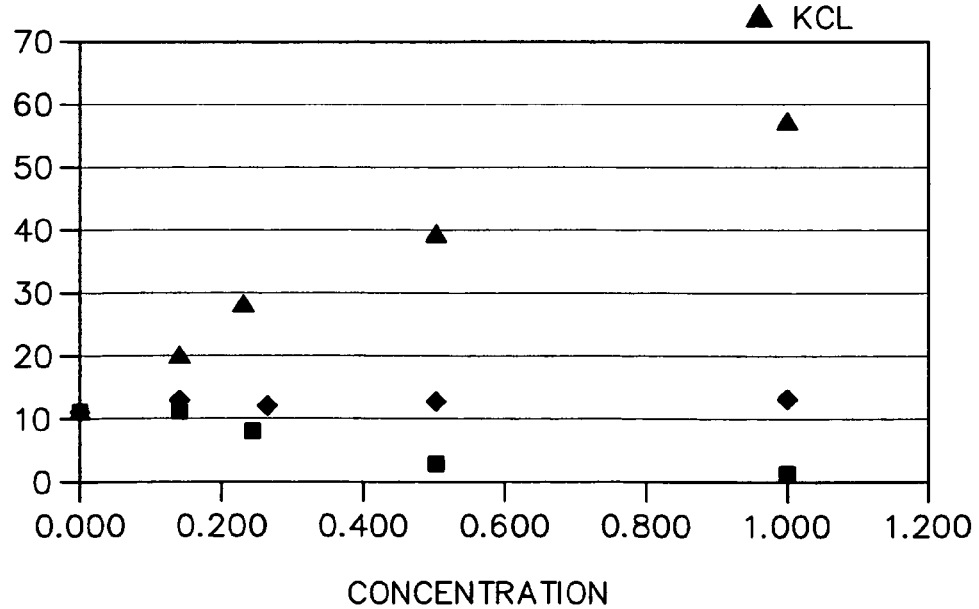
Figure 8C:
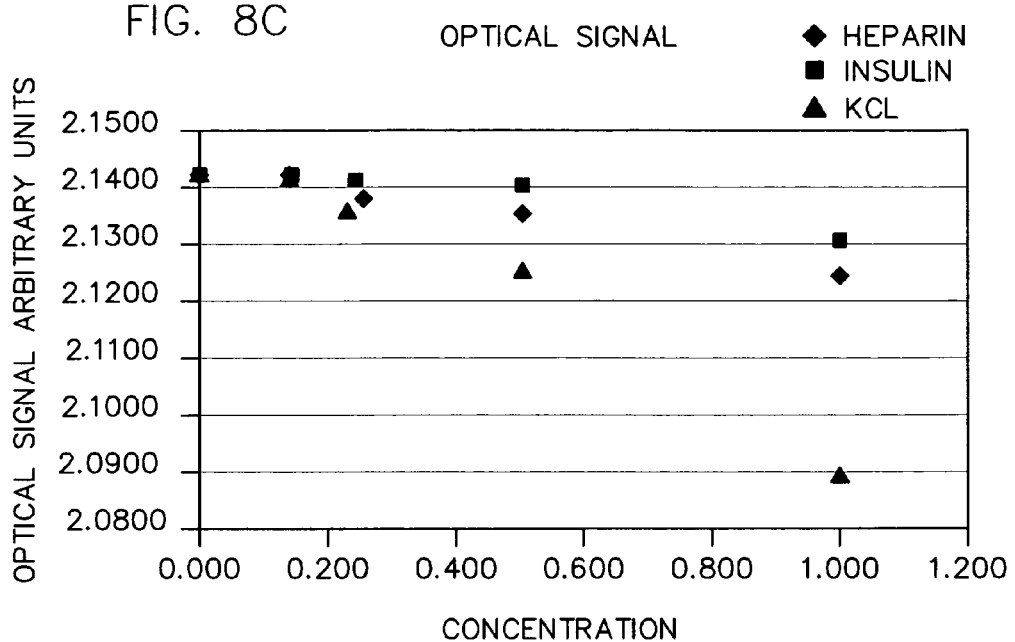
Figure 8D:
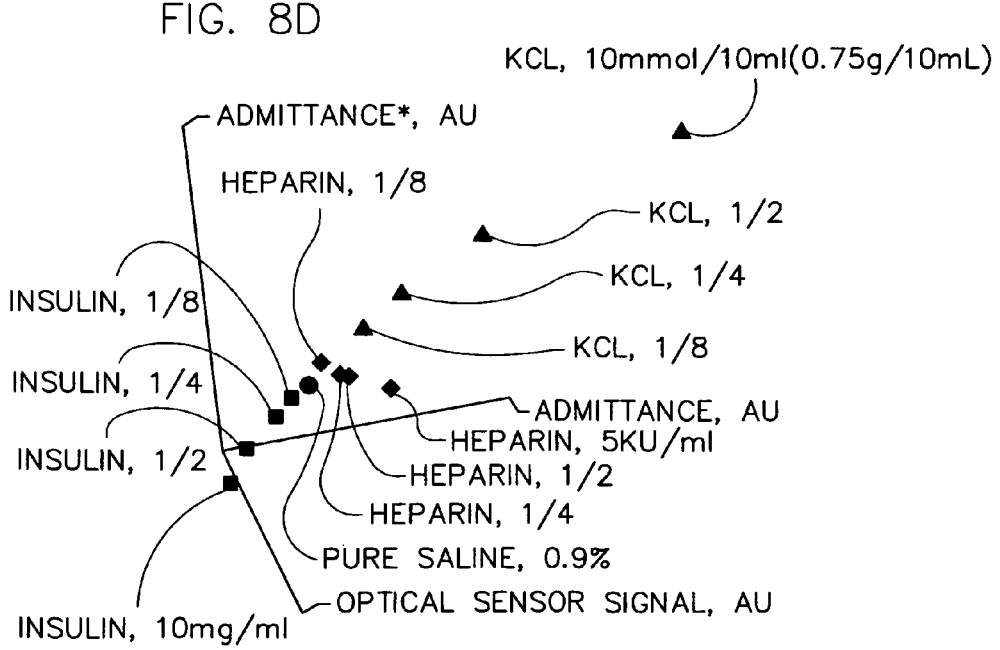

These results are also shown graphically in FIGS. 8(A-C) for measurements of admittance, real portion (FIG. 8A), admittance, imaginary portion (FIG. 8B), optical refractive index (FIG. 8C). A multi-parametric representation of such measurements is shown in FIG. 8D; the multi-parametric analysis and data demonstrate resolution of these various components at different concentrations.

Example 4

Identification of Intravenous Fluid Components with Multi-Channel Impedance Sensor A set of experiments were conducted using a multi-channel impedance sensor comprising two sensor elements. The two sensor elements each comprised a sensing surface defined by circular gold electrodes, 0.32 mm diameter, situated coplanar and at a distance of 0.75 mm from each other on a wall of a non-conductive flow path. An intravenous fluid consisting of 0.9% saline was provided in an infusion bag set on hanger. A fluid line assembly comprising an intravenous dripper was inserted, and flow from the infusion bag was initiated at a typical infusion rate (~120 cc/hr). The fluid line assembly comprised an injection port. The aforementioned gold electrode sensor elements were provided downstream from the injection port.

In this example, the sensor was used to measure the real and imaginary impedance of saline (0.90) flowing through the fluid line assembly at steady state. A bolus (1 ml) of saline-diluted potassium chloride (10 mg/ml) was injected into the flowing saline, and detected by the sensor. Independently and subsequently, a bolus (1 ml) of saline-diluted magnesium sulfate (40 mg/ml) was injected into the flowing saline and detected by the sensor. Independently and subsequently, a bolus of approximately 1 ml of plain deionized water was injected into the flowing saline, and detected by the sensor.

In each case, both in-phase and out-of-phase components of the current through the sensor were continuously recorded and plotted by the system. The real, in-phase component of the current was plotted along the X-axis and the imaginary, out-of-phase of the current was plotted along the Y-axis of the chart. Briefly, a 100 KHz AC voltage of 8 mV amplitude was applied across the electrodes in series with a 50 Ohm resistor, and the voltage drop across the resistor was measured using a Stanford Research Model SR830 lock-in amplifier. A microprocessor (a personal computer) was connected to the lock-in amplifier via RS232 interface with software recording the complex voltage read by the lock-in amplifier at a data sampling rate of approximately twice per second. The data was plotted with the real part of the measured voltage value along X-axis and the imaginary part—along Y-axis. In our experiments, an average $x_0+iy_0$ and standard deviation $\sigma$ were determined, accounting for naturally occurring noise. A measured voltage value $x+iy$ deviating from the average value by $|\Delta x+i\Delta y|>6\sigma$ in any direction on the XY chart is a statistically significant indication of a change in the fluid. In this case, $\arg(\Delta x+i\Delta y)$ defines the angular direction of the deviation vector. Two deviations $\Delta x_1+i\Delta y_1$, and $\Delta x_2+i\Delta y_2$ are statistically distinguishable if $|\Delta x_1+i\Delta y_1|>6\sigma$ and $|\Delta x_2+i\Delta y_2|>6\sigma$ and $|\Delta x_1-\Delta x_2+i(\Delta y_1-\Delta y_2)|>6\sigma$. The latter inequality defines the relationship between the magnitude of the deviations and the angle between them for the deviations to be distinguishable from each other.

Figure 9A:
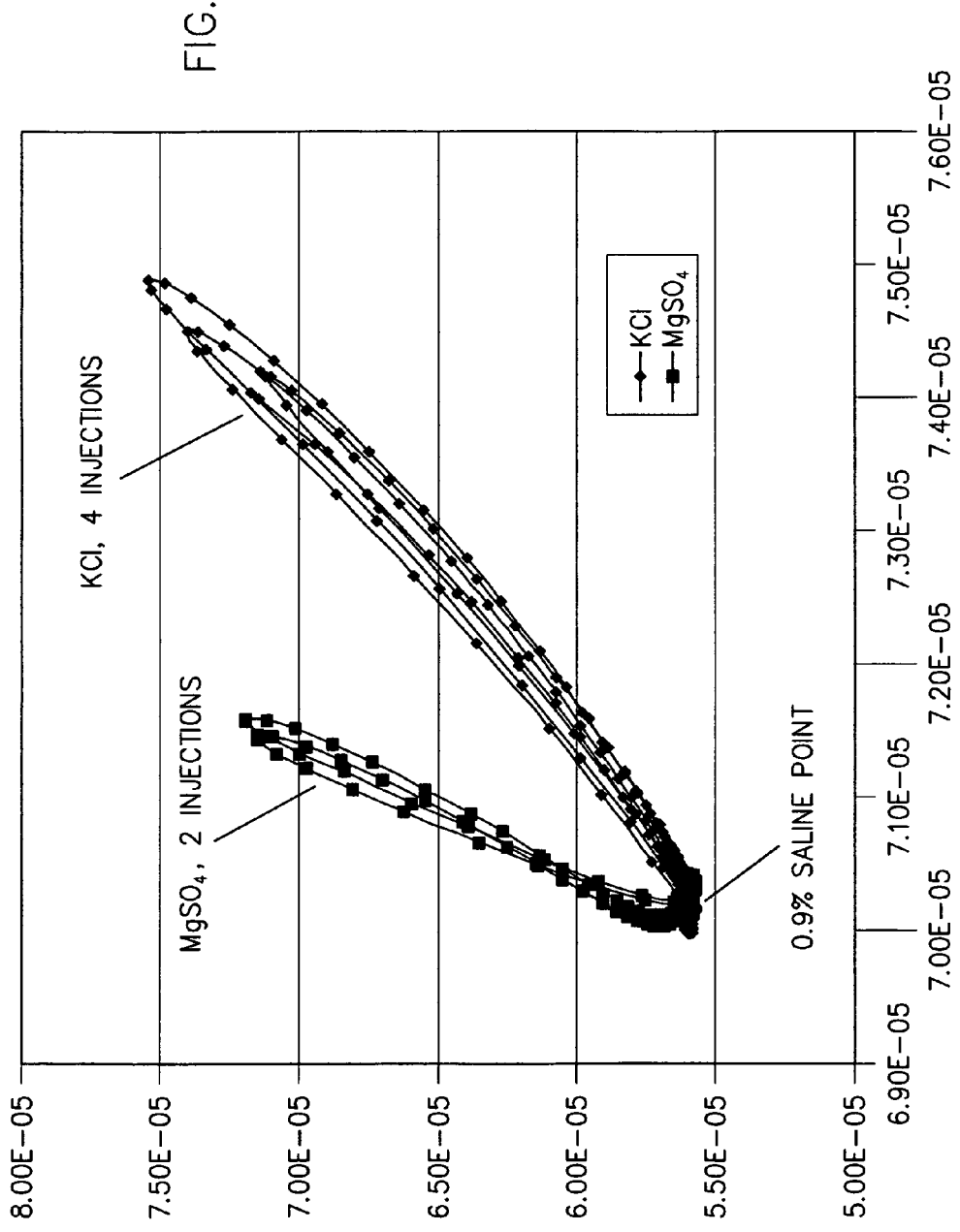
FIG. 9 (A-B) illustrate various data derived from Example 4, including plots of measurements of out-of-phase current (y-axis) and in-phase current (x-axis) for injections of potassium chloride (KCl) and magnesium sulfate (MgS04) (FIG. 9A), as well as for subsequent injections with water.

The values determined from the sensor in flowing saline resulted in substantially overlapping data points, as shown on the plot included as FIG. 9A.

The bolus of saline-diluted potassium chloride (KCl) injected into the saline flow through the injection port was detected by the sensor, resulting in a 2-dimensional characteristic signature for the KCl component. (See FIG. 9A). Multiple injections of potassium chloride (KCl) resulted in distinct substantially overlapping curves, as shown. Without being bound by theory not expressly recited in the claims, following injection of the saline-diluted potassium chloride into the flow as a bolus dose, the leading "front" edge of the flow profile for the bolus reaches the vicinity of the electrodes, and the complex current deviates from its average value in pure saline and returns back when trailing "back" edge of the flow profile for the bolus passes the vicinity of the electrodes, thereby producing the characteristic signature. One can observe that the leading edge of the potassium chloride injection produces deviation from the data point representing the saline and that such deviation is nearly linear and at a distance far greater than the 6a threshold of detection, thereby allowing for accurate determination of the direction of the deviation vector. For example, one can effect a linear regression of the measurement points from the 60 threshold of detection to the distance where residuals start exceeding 6a. For further results, one can also calculate an angle between X-axis and the directional vector of the deviation based on regression coefficients, which angle was found to be about 74.4° for potassium chloride under the conditions of this experiment.

The bolus of saline-diluted magnesium sulfate (MgS04) injected into the saline flow through the injection port was also detected by the sensor, resulting in a 2-dimensional characteristic signature of the MgS04 component—which was readily distinguishable from the signature for the KCl component. (See FIG. 9A) Multiple injections of magnesium sulfate (MgS04) resulted in distinct substantially overlapping curves, as shown. Without being bound by theory not expressly recited in the claims, the saline-diluted magnesium sulfate results in a unique characteristic signature which was differentiated from the data resulting from the potassium chloride. As seen in FIG. 9A, the deviation from the saline point is relatively more vertical and of a relatively smaller magnitude as compared to the deviation of potassium chloride. The angle of the initial deviation, calculated as explained above, was found to be 85.6° for the magnesium sulfate under the conditions of this experiment.

Figure 9B:
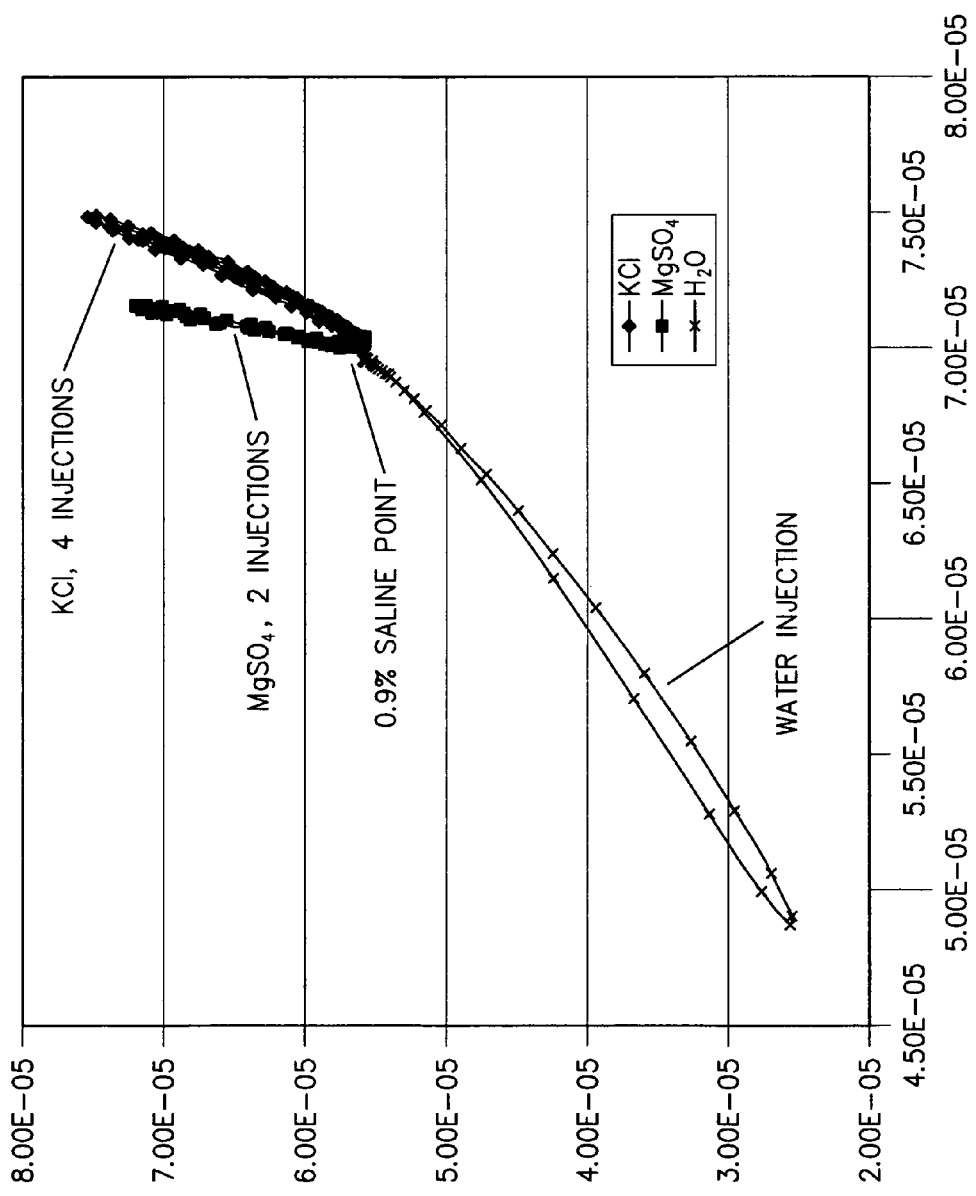

The bolus of deionized water injected into the saline flow through the injection port was likewise detected by the sensor, resulting in a 2-dimensional characteristic signature of the $H_2O$ component—which was readily distinguishable from both the signature for the KCl component and the signature of the $MgSO_4$ component, deviating in nearly the opposite direction therefrom. (See FIG. 9B) The angle of initial deviation for the water component as detected by the sensor was −118.2°.

In each case, the statistical uncertainty for the determined angles was estimated from the residuals of the linear regression used to calculate coefficients determining the angles, and for all three substances—potassium chloride, magnesium sulfide and water—was found to be ±0.62°.

These data demonstrate that highly diluted components injected into saline flow can be identified. Generally, deviation distance from a data point corresponding to pure saline depends on both concentration and molecular or ionic composition of the component, while deviation direction from such data point depends predominantly on the molecular or ionic composition of the component. For higher concentrations of the component, both magnitude and direction of the deviation become concentration-dependent in unique and distinguishable manner which is specific to and dependent upon the particular component added to the saline. Hence, such deviation dependencies enable identification of components having different compositions or concentrations.

Software can be used to identify potassium chloride, magnesium sulfide and water components within an intravenous saline fluid, based on the results of the afore-described experimental data. In one approach, for example, pattern recognition software can continuously observe voltage data derived from the sensor and check whether the value exceeds the 6a threshold. Once the threshold is exceeded, the software can indicate that a different substance is likely present in the flow and can start a linear regression on the consecutively measured points, checking whether residuals exceed the 6a threshold. The algorithm may, at that point, conclude that the linear section of the deviation curve was over, and may calculate a directional vector for the data set being reduced. The directional vector can be compared to vector values previously determined for specific components (e.g., pharmaceuticals) of interest. More specifically, for example, such analysis can be effected in terms of angles. For example, when the detected deviation corresponds to an angle of 74.4±0.62°—the software can identify the injected bolus as likely being potassium chloride. Similarly, for example, if the detected deviation corresponds to an angle of 85.6±0.62° or an angle of −118.2±0.62°, the software can identify injected substance as magnesium sulfate or deionized water, respectively. If the detected deviation angle does not correspond to angle for any known substances under the conditions of measurement, then the algorithm can report a detected unknown substance. Once a component is identified, a current cumulative dosing level can be measured by integrating either x or y or |Ax+/Ay| over time during the period defined from when the signal exceeded the detection threshold to the current time (e.g., taking into account the sensor sensitivity to identified substance and the volumetric flow).

Such pattern recognition algorithm can also be adapted to recognize other substances that are components of an intravenous fluid. Such substances will produce deviations in various directions, the angles for each of which can be determined as described above. In subsequent operation, such software can compare measured angles determined from detected data with the values for expected angles corresponding to certain substances, thereby identifying the substances. More elaborate pattern recognition algorithms can also be applied to the differentiation and recognition of data generated by the sensors in multidimensional space, as described in the specification. The various examples described herein are representative of, and not to be considered limiting of the inventions disclosed and claimed herein.

Tables 4A, 4B and 4C follow:

TABLE 4A

Heparin Dilution Series

| Heparin Relative Conc. | Optic | Admitt. | Admitt* |
|---|---|---|---|
| 1.000 | 2.1284 | 33.68978 | 14.12309 |
| 0.504 | 2.1390 | 29.85923 | 13.55784 |
| 0.248 | 2.1455 | 29.57476 | 13.1181 |
| 0.124, | 2.1432 | 26.91454 | 13.59039 |
| 0.000 | 2.1434 | 23.98381 | 10.90867 |

TABLE 4B

Insulin Dilution Series

| Insulin Relative Conc. | Optic | Admitt. | Admitt.* |
|---|---|---|---|
| 1.000 | 2.1313 | 6.59935 | 1.33295 |
| 0.503 | 2.1402 | 10.9246 | 3.14695 |
| 0.240 | 2.1424 | 17.6113 | 7.30539 |
| 0.126 | 2.1434 | 21.2221 | 10.3648 |
| 0.000 | 2.1434 | 23.9838 | 10.9087 |

TABLE 4C

Potassium Chloride Dilution Series

| KCL Relative Conc. | Optic | Admitt. | Admitt.* |
|---|---|---|---|
| 1.000 | 2.0889 | 66.51804 | 57.43262 |
| 0.496 | 2.2158 | 54.16412 | 39.15326 |
| 0.221 | 2.1360 | 42.24291 | 27.72464 |
| 0.123 | 2.1420 | 36.42675 | 20.27508 |
| 0.000 | 2.1434 | 23.98381 | 10.90867 |

What is claimed is:

1. A method for determining an identity and a concentration of an intravenous fluid by detecting fluid interactions at first and second sensing surfaces, the method comprising:
    contacting the first and second sensing surfaces of a sensor of a device for multi-parametric testing of the intravenous fluid to the intravenous fluid;
    determining a multi-parametric profile from the intravenous fluid, wherein the multi-parametric profile comprises
        a first parameter detecting the fluid interactions at the first sensing surface, the first parameter comprising a complex admittance or impedance signal from the intravenous fluid, and
        a second parameter detecting the fluid interactions at the second sensing surface, wherein the second parameter is independent of the first parameter;
    comparing the multi-parametric profile to stored expected parameter values to determine an identity and a concentration of one or more components of the intravenous fluid.

2. The method of claim 1, wherein the step of comparing the multi-parametric profile comprises simultaneously identifying and determining the concentration of the one or more components of the intravenous fluid.

3. The method of claim 1, wherein the step of determining the multi-parametric profile comprises measuring an optical parameter.

4. The method of claim 1, wherein the first parameter comprises an electrical admittance or impedance measurement taken at a plurality of frequencies.

5. A method for determining an identity and a concentration of an intravenous fluid by detecting fluid interactions at first and second sensing surfaces, the method comprising:
contacting the intravenous fluid to the first and second sensing surfaces of a device for multi-parametric testing of the intravenous fluid;
determining a multi-parametric profile from the intravenous fluid, wherein the multi-parametric profile comprises
a first parameter detecting the fluid interactions at the first sensing surface, the first parameter comprises a first complex admittance or impedance signal from the intravenous fluid, and
a second parameter detecting the fluid interactions at the second sensing surface, wherein the second parameter comprises a second complex admittance or impedance signal from the intravenous fluid;
comparing the first and second parameters of the multi-parametric profile to stored expected parameter values to identify and determine a concentration of one or more components of the intravenous fluid.

6. The method of claim 5, wherein the first parameter comprises an admittance or impedance spectrum taken at a plurality of frequencies.

7. The method of claim 5, wherein the second parameter comprises an admittance or impedance spectrum taken at a plurality of frequencies.

8. The method of claim 5, wherein the step of determining the multi-parametric profile comprises determining a third parameter that is not a complex admittance or impedance signal.

9. The method of claim 8 wherein the third parameter is an optical parameter.

10. The method of claim 5, further comprising connecting the device for multi-parametric testing of the intravenous fluid to an intravenous infusion device for infusion of the fluid into a vascular system of a patient.

11. A method for determining an identity and a concentration of an intravenous fluid by detecting fluid interactions at first and second sensing surfaces, the method comprising:
applying the intravenous fluid to the first and second sensing surfaces of a device for testing of the intravenous fluid by admittance or impedance spectroscopy;
determining complex admittance or impedance signals from the intravenous fluid between a first pair of electrodes by detecting the fluid interactions at the first sensing surface;
determining complex admittance or impedance signals from the intravenous fluid between a second pair of electrodes by detecting the fluid interactions at the second sensing surface, and
comparing received parameter values incorporating the complex admittance or impedance signals with stored expected parameter values to identify and determine a concentration of one or more components of the intravenous fluid.

12. The method of claim 11, wherein the complex admittance or impedance signals comprise an admittance or impedance spectrum taken at a plurality of frequencies.

13. The method of claim 11, further comprising applying the intravenous fluid into a vascular system of a patient.

14. The method of claim 11, further comprising connecting the device to an intravenous infusion device for infusion of the fluid into a vascular system of a patient.

* * * * *